US010624953B2

(12) United States Patent
Arce

(10) Patent No.: US 10,624,953 B2
(45) Date of Patent: *Apr. 21, 2020

(54) HUMAN-DERIVED RECOMBINANT FSH FOR CONTROLLED OVARIAN STIMULATION

(71) Applicant: Ferring B.V., Hoofddorp (NL)

(72) Inventor: Joan-Carles Arce, Dragør (DK)

(73) Assignee: FERRING B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,962

(22) Filed: Jun. 29, 2017

(65) Prior Publication Data

US 2018/0028620 A1 Feb. 1, 2018

Related U.S. Application Data

(63) Continuation of application No. 14/237,697, filed as application No. PCT/EP2012/065507 on Aug. 8, 2012, now Pat. No. 9,694,052.

(30) Foreign Application Priority Data

Aug. 8, 2011 (EP) .................................. 11176803

(51) Int. Cl.
*A61K 38/24* (2006.01)

(52) U.S. Cl.
CPC .................................. *A61K 38/24* (2013.01)

(58) Field of Classification Search
None
See application file for complete search history.

(56) References Cited

U.S. PATENT DOCUMENTS

| 7,964,562 B2 | 6/2011 | Filicori |
| 8,951,967 B2 | 2/2015 | Cottingham et al. |
| 8,993,732 B2 | 3/2015 | Sjögren et al. |
| 2008/0108571 A1 | 5/2008 | Filicori |
| 2015/0065695 A1 | 3/2015 | Cottingham et al. |

FOREIGN PATENT DOCUMENTS

| JP | 2005-515974 | 6/2005 |
| JP | 2011-519359 | 7/2011 |
| WO | WO2009/127826 | 10/2009 |
| WO | WO2012/017058 | 2/2012 |
| WO | WO 2012/042381 | 4/2012 |

OTHER PUBLICATIONS

Dewailly et al., Human Reproduction, 2011; 26: 3123-3129 (Year: 2011).*
Chin et al., Cytotechnology, 1996; 21: 171-182 (Year: 1996).*
U.S. Appl. No. 14/631,382, filed Feb. 25, 2015, Sjorgen and Bagger.
"Revised American Society for Reproductive Medicine classification of endometriosis: 1996," Fertil. Steril., May 1997, 67(5): 817-821.
Anckaert et al., "The value of anti-Mullerian hormone measurement in the long GnRH agonist protocol: association with ovarian response and gonadotrophin-dose adjustments," Human Reproduction, 2012, 27(6): 1829-1839.
Andersen et al., "FSH isoform composition of commercial gonadotrophin preparations: a neglected aspect?," Reprod Biomed Online, Aug. 2004, 9(2): 231-236.
Arey et al., "Induction of promiscuous G protein coupling of the follicle-stimulating hormone (FSH) receptor: a novel mechanism for transducing pleiotropic actions of FSH isoforms," Mol Endocrinol, May 1997, 11(5): 517-526.
Baenziger and Green, "Pituitary glycoprotein hormone oligosaccharides: structure, synthesis and function of the asparagine-linked oligosaccharides on lutropin, follitropin and thyrotropin," Biochim Biophys Acta, Jun. 1988, 947(2): 287-306.
Bassett and Driebergen, "Continued improvements in the quality and consistency of follitropin alfa, recombinant human FSH," Reprod Biomed Online, Feb. 2005, 10(2): 169-77.
Broer et al., "AMH and AFC as predictors of excessive response in controlled ovarian hyperstimulation: a meta-analysis," Human Reproduction Update, 2011, 17(1): 46-54.
D'Antonio et al., "Biological characterization of recombinant human follicle stimulating hormone isoforms," Hum Reprod, May 1999, 14(5): 1160-1167.
Dalpathado et al., "Comparative glycomics of the glycoprotein follicle stimulating hormone: glycopeptide analysis of isolates from two mammalian species," Biochemistry, Jul. 2006, 45(28): 8665-73.
Damian-Matsumura et al., "Oestrogens regulate pituitary alpha2,3-sialyltransferase messenger ribonucleic acid levels in the female rat," J Mol Endocrinol, Oct. 1999, 23(2): 153-165.
de Leeuw et al., "Structure-function relationship of recombinant follicle stimulating hormone (Puregon)," Mol Hum Reprod, May 1996, 2(5): 361-9.
Dias and Van Roey, "Structural biology of human follitropin and its receptor," Arch Med Res, 2001, 32(6): 510-9.
Ferring Pharmaceuticals, "A Randomised, Controlled, Assessor-blind, Parallel Groups, Multi-national, Multi-centre Trial Assessing the Dose-response Relationship of FE 999049 in Controlled Ovarian Stimulation in Women Undergoing an ART Programme," Aug. 30, 2011, [retrieved on Jul. 9, 2015], Retrieved from the internet: URLhttps://clinicaltrials.gov/ct2/show/NCT01426386?term=fe+999049&rank=1, 3 pages.
Fiddes and Goodman, "Isolation, cloning and sequence analysis of the cDNA for the alpha-subunit of human chorionic gonadotropin," Nature, Oct. 1979, 281(5730): 351-356.
Flack et al., "Increased biological activity due to basic isoforms in recombinant human follicle-stimulating hormone produced in a human cell line," J Clin Endocrinol Metab, Sep. 1994, 79(3): 756-60.
Fox et al., "Three-dimensional structure of human follicle-stimulating hormone," Mol Endocrinol, Mar. 2001, 15(3): 378-89.
Freiesleben et al., "Individual versus standard dose of rFSH in a mild stimulation protocol for intrauterine insemination: a randomized study," Human Reproduction, 2009, 1-8.

(Continued)

*Primary Examiner* — Christina M Borgeest
(74) *Attorney, Agent, or Firm* — Foley & Lardner LLP

(57) ABSTRACT

Preparations including FSH, for example recombinant FSH, for use in the treatment of infertility.

15 Claims, 6 Drawing Sheets

Specification includes a Sequence Listing.

(56) References Cited

OTHER PUBLICATIONS

Freiesleben et al., "Prospective investigation of serum anti-Müllerian hormone concentration in ovulatory intrauterine insemination patients: a preliminary study," Reprod Biomed Online, May 2010, 20(5): 582-587.
Grabenhorst et al., "Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal(beta 1-4)GlcNAc(beta 1-2)Man(alpha 1-3)-branch of diantennary oligosaccharides from secreted recombinant beta-trace protein," Eur J Biochem, Sep. 1995, 232(3): 718-725.
Green and Baenziger, "Asparagine-linked Oligosaccharides on Lutropin, Follitropin, and Thyrostopin," The Journal of Biological Chemistry, Jan. 1988, 263(1): 25-35.
Grundmann et al., "Complete cDNA sequence encoding human β-galactoside α-2,6-sialyltransferase," Nucleic Acids Research, 1990, 18(3): 667.
Hard et al., "Solution structure of the glucocorticoid receptor DNA-binding domain," Science, Jul. 13, 1990, 249(4965):157-160.
Howles, "Genetic engineering of human FSH (Gonal-F)," Human Reprod Update, Mar. 1996, 2(2): 172-91.
Hugues, RBM Online, 2002; 6: 185-190.
Kagawa et al., "Comparative study of asparagine-linked sugar chains of natural human interferon-beta 1 and recombinant human interferon-beta 1 produced by three different mammalian cells," J Biol Chem, Nov. 1968, 263(33): 17508-17515.
Keene et al., "Expression of Biologically Active Human Follitropin in Chinese Hamster Ovary Cells," The Journal of Biological Chemistry, Mar. 1989, 264(9): 4769-4775.
Kitagawa and Paulson, "Cloning of a novel alpha 2,3-sialyltransferase that sialylates glycoprotein and glycolipid carbohydrate groups," J Biol Chem, Jan. 1994, 269(2): 1394-401.
Kucuk et al., J Obstet Gynaecol Res. 2008; 34: 574-7.
Lee et al., "Alteration of terminal glycosylation sequences on N-linked oligosaccharides of Chinese hamster ovary cells by expression of beta-galactoside alpha 2,6-sialyltransferase," J Biol Chem, Aug. 1989, 264(23): 13848-55.
Lekamge, J Assit Reprod Genet. 2008; 25; 515-521.
Lowry et al., "Protein measurement with the Folin phenol reagent," J Biol Chem, Nov. 1951, 193(1): 265-75.
Lowry et al., "Purification of anterior pituitary and hypothalamic hormones," J Clin Pathol Suppl, 1976, 7: 16-21.
Nelson et al., "Anti-Mullerian hormone-based approach to controlled ovarian stimulation for assisted conception," Human Reproduction, 2009, 1(1): 1-9.
Nelson et al., Human Reproduction, 2009; 24; 867-875; advanced access publication on Jan. 10, 2009; doi: 10.1093/humrep/den480.
Olivennes et al., "Individualizing FSH dose for assisted reproduction using a novel algorithm: the CONSORT study," Reprod Biomed Online, Feb. 2009, 18(2): 195-204.
Pierce and Parsons, "Glycoprotein hormones: structure and function," Annu Rev Biochem, 1981, 50: 465-95.
Pricer and Ashwell, "The binding of desialylated glycoproteins by plasma membranes of rat liver," J Biol Chem, Aug. 1971, 246(15): 4825-33.
Rathnam and Saxena, "Primary amino acid sequence of follicle-stimulating hormone from human pituitary glands. I. alpha subunit," J Biol Chem, Sep. 1975, 250(17): 6735-46.
Regoeczi et al., "Elimination of asialofetuin and asialoorosomucoid by the intact rat. Quantitative aspects of the hepatic clearance mechanism," Biochim Biophys Acta, Jul. 1978, 541(3): 372-84.
Royle et al., "Methods in Molecular Biology," 347:, 125-143, 2007.
Ryan et al., "Structure-function relationships of gonadotropins," Recent Prog Horm Res, 1987, 43: 383-429.
Saxena and Rathnam, "Amino acid sequence of the beta subunit of follicle-stimulating hormone from human pituitary glands," J Biol Chem, Feb. 1976, 251(4): 993-1005.
Steelman and Pohley, "Assay of the follicle stimulating hormone based on the augmentation with human chorionic gonadotropin," Endocrinology, Dec. 1953, 53(6): 604-616.
Steer and Ashwell, "Studies on a mammalian hepatic binding protein specific for asialoglycoproteins. Evidence for receptor recycling in isolated rat hepatocytes," J Biol Chem, Apr. 1980, 255(7): 3008-13.
Svensson et al., "Organization of the beta-galactoside alpha 2,6-sialyltransferase gene. Evidence for the transcriptional regulation of terminal glycosylation," J Biol Chem, Dec. 1990, 265(34): 20863-8.
Takentani et al., Reprod Med Biol. 2010; 9; 91-97.
Takeuchi et al., "Comparative study of the asparagine-linked sugar chains of human erythropoietins purified from urine and the culture medium of recombinant Chinese hamster ovary cells," J Biol Chem, Mar. 1988, 263(8): 3657-63.
Timossi et al., "A naturally occurring basically charged human follicle-stimulating hormone (FSH) variant inhibits FSH-induced androgen aromatization and tissue-type plasminogen activator enzyme activity in vitro," Neuroendocrinology, Mar. 1998, 67(3): 153-63.
Timossi et al., "Differential effects of the charge variants of human follicle-stimulating hormone," J Endocrinol, May 2000, 165(2): 193-205.
Ulloa-Aguirre et al., "Biological characterization of the naturally occurring analogues of intrapituitary human follicle-stimulating hormone," Hum Reprod, Jan. 1992, 7(1): 23-30.
Ulloa-Aguirre et al., "Endocrine regulation of gonadotropin glycosylation," Arch Med Res, Nov. 2001, 32(6): 520-32.
Ulloa-Aguirre et al., "Follicle-stimulating isohormones: characterization and physiological relevance," Endocr Rev, Dec. 1995, 16(6): 765-87.
Ulloa-Aguirre et al., "Immunological and biological potencies of the different molecular species of gonadotrophins," Hum Reprod, May 1988, 3(4): 491-501.
Ulloa-Aguirre et al., "Impact of carbohydrate heterogeneity in function of follicle-stimulating hormone: studies derived from in vitro and in vivo models," Biol Reprod, Aug. 2003, 69(2): 379-89.
Van Lenten and Ashwell, "The binding of desialylated glycoproteins by plasma membranes of rat liver. Development of a quantitative inhibition assay," J Biol Chem, Jul. 1972, 247(14): 4633-40.
Wide and Albertsson-Wikland, "Change in Electrophoretic Mobility of Human Follicle-Stimulating Hormone in Serum after Administration of Gonadotropin-Releasing Hormone," J. Clin. Endocrin. & Metabol., Jul. 1, 2013, 70(1):271-276.
Wide and Bakos, "More basic forms of both human follicle-stimulating hormone and luteinizing hormone in serum at midcycle compared with the follicular of luteal phase" J Clin Endocrinol Metab, Apr. 1993, 76(4): 885-9.
Wide et al., "Sulfonation and sialylation of gonadotropins in women during the menstrual cycle, after menopause, and with polycystic ovarian syndrome and in men," J Clin Endocrinol Metab, Nov. 2007, 92(11): 4410-7.
Zambrano et al., "Receptor binding activity and in vitro biological activity of the human FSH charge isoforms as disclosed by heterologous and homologous assay systems," Endocrine, Apr. 1999, 10(2):113-121.
Zhang et al., "Stable expression of human alpha-2,6-sialyltransferase in Chinese hamster ovary cells: functional consequences for human erythropoietin expression and bioactivity," Biochim Biophys Acta, Nov. 1998, 1425(3): 441-52.

* cited by examiner

SEQUENCE LISTING

<160> NUMBER OF SEQ ID NOS: 16

<210> SEQ ID NO 1
<211> LENGTH: 351
<212> TYPE: DNA
<213> ORGANISM: Homo sapiens

<400> SEQUENCE: 1

```
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
```

| tatcccactc cactaaggtc caagaagacg atgttggtcc aaaagaacgt cacctcagag | 240 |
| tccacttgct gtgtagctaa atcatataac agggtcacag taatgggggg tttcaaagtg | 300 |
| gagaaccaca cggcgtgcca ctgcagtact tgttattatc acaaatctta a | 351 |

<210> SEQ ID NO 2
<211> LENGTH: 390
<212> TYPE: DNA
<213> ORGANISM: Homo sapiens

<400> SEQUENCE: 2

| atgaagacac tccagttttt cttccttttc tgttgctgga aagcaatctg ctgcaatagc | 60 |
| tgtgagctga ccaacatcac cattgcaata gagaaagaag aatgtcgttt ctgcataagc | 120 |
| atcaacacca cttggtgtgc tggctactgc tacaccaggg atctggtgta taaggaccca | 180 |
| gccaggccca aaatccagaa acatgtacc ttcaaggaac tggtatatga acagtgaga | 240 |
| gtgcccggct gtgctcacca tgcagattcc ttgtatacat acccagtggc cacccagtgt | 300 |
| cactgtggca gtgtgacag cgacagcact gattgtactg tgcgaggcct ggggcccagc | 360 |
| tactgctcct ttggtgaaat gaaagaataa | 390 |

<210> SEQ ID NO 3
<211> LENGTH: 999
<212> TYPE: DNA
<213> ORGANISM: Homo sapiens

<400> SEQUENCE: 3

| atgtgtcctg caggctggaa gctcctggcc atgttggctc tggtcctggt cgtcatggtg | 60 |
| tggtattcca tctcccggga agacaggtac atcgagcttt tttattttcc catcccagag | 120 |
| aagaaggagc cgtgcctcca gggtgaggca gagagcaagg cctctaagct ctttggcaac | 180 |
| tactcccggg atcagcccat cttcctgcgg cttgaggatt atttctgggt caagacgcca | 240 |
| tctgcttacg agctgcccta tgggaccaag gggagtgagg atctgctcct ccgggtgcta | 300 |
| gccatcacca gctcctccat ccccaagaac atccagagcc tcaggtgccg ccgctgtgtg | 360 |
| gtcgtgggga cgggcaccg gctgcggaac agctcactgg gagatgccat caacaagtac | 420 |
| gatgtggtca tcagattgaa caatgcccca gtggctggct atgagggtga cgtgggctcc | 480 |
| aagaccacca tgcgtctctt ctaccctgaa tctgcccact tcgacccaa agtagaaaac | 540 |
| aacccagaca cactcctcgt cctggtagct ttcaaggcaa tggacttcca ctggattgag | 600 |
| accatcctga gtgataagaa gcgggtgcga aagggtttct ggaaacagcc tccctcatc | 660 |
| tgggatgtca atcctaaaca gattcggatt ctcaacccct tcttcatgga gattgcagct | 720 |
| gacaaactgc tgagcctgcc aatgcaacag ccacggaaga ttaagcagaa gcccaccacg | 780 |
| ggcctgttgg ccatcacgct ggccctccac ctctgtgact tggtgcacat tgccggcttt | 840 |
| ggctacccag acgcctacaa caagaagcag accattcact actatgagca gatcacgctc | 900 |
| aagtccatgg cggggtcagg ccataatgtc tcccaagagg ccctggccat taagcggatg | 960 |
| ctggagatgg gagctatcaa gaacctcacg tccttctga | 999 |

<210> SEQ ID NO 4
<211> LENGTH: 1221
<212> TYPE: DNA
<213> ORGANISM: Homo sapiens

<400> SEQUENCE: 4

```
atgattcaca ccaacctgaa gaaaaagttc agctgctgcg tcctggtctt tcttctgttt      60
gcagtcatct gtgtgtggaa ggaaaagaag aaagggagtt actatgattc ctttaaattg     120
caaaccaagg aattccaggt gttaaagagt ctggggaaat tggccatggg gtctgattcc     180
cagtctgtat cctcaagcag cacccaggac cccacaggg gccgccagac cctcggcagt      240
ctcagaggcc tagccaaggc caaccagag gcctccttcc aggtgtggaa caaggacagc      300
tcttccaaaa accttatccc taggctgcaa aagatctgga gaattaccct aagcatgaac     360
aagtacaaag tgtcctacaa ggggccagga ccaggcatca agttcagtgc agaggccctg     420
cgctgccacc tccgggacca tgtgaatgta ccatggtag aggtcacaga ttttcccttc      480
aatacctctg aatgggaggg ttatctgccc aaggagagca ttaggaccaa ggctgggcct     540
tggggcaggt gtgctgttgt gtcgtcagcg ggatctctga agtcctccca actaggcaga     600
gaaatcgatg atcatgacgc agtcctgagg tttaatgggg cacccacagc caacttccaa     660
caagatgtgg gcacaaaaac taccattcgc ctgatgaact ctcagttggt taccacagag     720
aagcgcttcc tcaaagacag tttgtacaat gaaggaatcc taattgtatg ggacccatct     780
gtataccact cagatatccc aaagtggtac cagaatccgg attataattt ctttaacaac     840
tacaagactt atcgtaagct gcaccccaat cagcccttt acatcctcaa gccccagatg     900
ccttgggagc tatgggacat tcttcaagaa atctccccag aagagattca gccaaacccc     960
ccatcctctg ggatgcttgg tatcatcatc atgatgacgc tgtgtgacca ggtggatatt    1020
tatgagttcc tcccatccaa gcgcaagact gacgtgtgct actactacca gaagttcttc    1080
gatagtgcct gcacgatggg tgcctaccac ccgctgctct atgagaagaa tttggtgaag    1140
catctcaacc agggcacaga tgaggacatc tacctgcttg aaaagccac actgcctggc     1200
ttccggacca ttcactgcta a                                              1221
```

<210> SEQ ID NO 5
<211> LENGTH: 116
<212> TYPE: PRT
<213> ORGANISM: Homo sapiens

<400> SEQUENCE: 5

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
             20                  25                  30

Glu Cys Thr Leu Gln Glu Asn Pro Phe Phe Ser Gln Pro Gly Ala Pro
         35                  40                  45

Ile Leu Gln Cys Met Gly Cys Cys Phe Ser Arg Ala Tyr Pro Thr Pro
     50                  55                  60

Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
                 85                  90                  95

Gly Phe Lys Val Glu Asn His Thr Ala Cys His Cys Ser Thr Cys Tyr
            100                 105                 110

Tyr His Lys Ser
        115
```

```
<210> SEQ ID NO 6
<211> LENGTH: 129
<212> TYPE: PRT
<213> ORGANISM: Homo sapiens

<400> SEQUENCE: 6

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu

<210> SEQ ID NO 7
<211> LENGTH: 332
<212> TYPE: PRT
<213> ORGANISM: Homo sapiens

<400> SEQUENCE: 7

Met Cys Pro Ala Gly Trp Lys Leu Leu Ala Met Leu Ala Leu Val Leu
1               5                   10                  15

Val Val Met Val Trp Tyr Ser Ile Ser Arg Glu Asp Arg Tyr Ile Glu
            20                  25                  30

Leu Phe Tyr Phe Pro Ile Pro Glu Lys Lys Glu Pro Cys Leu Gln Gly
        35                  40                  45

Glu Ala Glu Ser Lys Ala Ser Lys Leu Phe Gly Asn Tyr Ser Arg Asp
    50                  55                  60

Gln Pro Ile Phe Leu Arg Leu Glu Asp Tyr Phe Trp Val Lys Thr Pro
65                  70                  75                  80

Ser Ala Tyr Glu Leu Pro Tyr Gly Thr Lys Gly Ser Glu Asp Leu Leu
                85                  90                  95

Leu Arg Val Leu Ala Ile Thr Ser Ser Ile Pro Lys Asn Ile Gln
            100                 105                 110

Ser Leu Arg Cys Arg Arg Cys Val Val Val Gly Asn Gly His Arg Leu
        115                 120                 125

Arg Asn Ser Ser Leu Gly Asp Ala Ile Asn Lys Tyr Asp Val Val Ile
    130                 135                 140

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
            180                 185                 190

Ala Met Asp Phe His Trp Ile Glu Thr Ile Leu Ser Asp Lys Lys Arg
        195                 200                 205
```

```
Val Arg Lys Gly Phe Trp Lys Gln Pro Pro Leu Ile Trp Asp Val Asn
    210             215                 220
Pro Lys Gln Ile Arg Ile Leu Asn Pro Phe Met Glu Ile Ala Ala
225             230                 235                 240
Asp Lys Leu Leu Ser Leu Pro Met Gln Gln Pro Arg Lys Ile Lys Gln
                245                 250                 255
Lys Pro Thr Thr Gly Leu Leu Ala Ile Thr Leu Ala Leu His Leu Cys
            260                 265                 270
Asp Leu Val His Ile Ala Gly Phe Gly Tyr Pro Asp Ala Tyr Asn Lys
                275                 280                 285
Lys Gln Thr Ile His Tyr Tyr Glu Gln Ile Thr Leu Lys Ser Met Ala
        290                 295                 300
Gly Ser Gly His Asn Val Ser Gln Glu Ala Leu Ala Ile Lys Arg Met
305             310                 315                 320
Leu Glu Met Gly Ala Ile Lys Asn Leu Thr Ser Phe
                325                 330
```

<210> SEQ ID NO 8
<211> LENGTH: 406
<212> TYPE: PRT
<213> ORGANISM: Homo sapiens

<400> SEQUENCE: 8

```
Met Ile His Thr Asn Leu Lys Lys Lys Phe Ser Cys Cys Val Leu Val
1               5                   10                  15
Phe Leu Leu Phe Ala Val Ile Cys Val Trp Lys Glu Lys Lys Lys Gly
                20                  25                  30
Ser Tyr Tyr Asp Ser Phe Lys Leu Gln Thr Lys Glu Phe Gln Val Leu
            35                  40                  45
Lys Ser Leu Gly Lys Leu Ala Met Gly Ser Asp Ser Gln Ser Val Ser
50              55                  60
Ser Ser Ser Thr Gln Asp Pro His Arg Gly Arg Gln Thr Leu Gly Ser
65              70                  75                  80
Leu Arg Gly Leu Ala Lys Ala Lys Pro Glu Ala Ser Phe Gln Val Trp
                85                  90                  95
Asn Lys Asp Ser Ser Lys Asn Leu Ile Pro Arg Leu Gln Lys Ile
                100                 105                 110
Trp Lys Asn Tyr Leu Ser Met Asn Lys Tyr Lys Val Ser Tyr Lys Gly
            115                 120                 125
Pro Gly Pro Gly Ile Lys Phe Ser Ala Glu Ala Leu Arg Cys His Leu
130             135                 140
Arg Asp His Val Asn Val Ser Met Val Glu Val Thr Asp Phe Pro Phe
145             150                 155                 160
Asn Thr Ser Glu Trp Glu Gly Tyr Leu Pro Lys Glu Ser Ile Arg Thr
                165                 170                 175
Lys Ala Gly Pro Trp Gly Arg Cys Ala Val Val Ser Ser Ala Gly Ser
            180                 185                 190
Leu Lys Ser Ser Gln Leu Gly Arg Glu Ile Asp Asp His Asp Ala Val
        195                 200                 205
Leu Arg Phe Asn Gly Ala Pro Thr Ala Asn Phe Gln Gln Asp Val Gly
    210                 215                 220
Thr Lys Thr Thr Ile Arg Leu Met Asn Ser Gln Leu Val Thr Thr Glu
225                 230                 235                 240
Lys Arg Phe Leu Lys Asp Ser Leu Tyr Asn Glu Gly Ile Leu Ile Val
                245                 250                 255
```

```
Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
        370                 375                 380

Gly Thr Asp Glu Asp Ile Tyr Leu Leu Gly Lys Ala Thr Leu Pro Gly
385                 390                 395                 400

Phe Arg Thr Ile His Cys
                405
```

<210> SEQ ID NO 9
<211> LENGTH: 39
<212> TYPE: DNA
<213> ORGANISM: Artificial Sequence
<220> FEATURE:
<223> OTHER INFORMATION: PCR primer FSHa-fw

<400> SEQUENCE: 9
ccaggatccg ccaccatgga ttactacaga aaaatatgc                                39

<210> SEQ ID NO 10
<211> LENGTH: 31
<212> TYPE: DNA
<213> ORGANISM: Artificial Sequence
<220> FEATURE:
<223> OTHER INFORMATION: PCR primer FSHa-rev

<400> SEQUENCE: 10
ggatggctag cttaagattt gtgataataa c                                        31

<210> SEQ ID NO 11
<211> LENGTH: 35
<212> TYPE: DNA
<213> ORGANISM: Artificial Sequence
<220> FEATURE:
<223> OTHER INFORMATION: PCR primer FSHb-fw

<400> SEQUENCE: 11
ccaggcgcgc caccatgaag acactccagt ttttc                                    35

<210> SEQ ID NO 12
<211> LENGTH: 36
<212> TYPE: DNA
<213> ORGANISM: Artificial Sequence
<220> FEATURE:
<223> OTHER INFORMATION: PCR primer FSHb-rev

<400> SEQUENCE: 12
ccgggttaac ttattattct ttcatttcac caaagg                                   36

```
<210> SEQ ID NO 13
<211> LENGTH: 37
<212> TYPE: DNA
<213> ORGANISM: Artificial Sequence
<220> FEATURE:
<223> OTHER INFORMATION: PCR primer 2,3STfw

<400> SEQUENCE: 13
ccaggatccg ccaccatgtg tcctgcaggc tggaagc                                37

<210> SEQ ID NO 14
<211> LENGTH: 35
<212> TYPE: DNA
<213> ORGANISM: Artificial Sequence
<220> FEATURE:
<223> OTHER INFORMATION: PCR primer 2,3STrev

<400> SEQUENCE: 14
tttttttctt aagtcagaag gacgtgaggt tcttg                                  35

<210> SEQ ID NO 15
<211> LENGTH: 36
<212> TYPE: DNA
<213> ORGANISM: Artificial Sequence
<220> FEATURE:
<223> OTHER INFORMATION: PCR primer 2,6STfw

<400> SEQUENCE: 15
ccaggatccg ccaccatgat tcacaccaac ctgaag                                 36

<210> SEQ ID NO 16
<211> LENGTH: 32
<212> TYPE: DNA
<213> ORGANISM: Artificial Sequence
<220> FEATURE:
<223> OTHER INFORMATION: PCR primer 2,6STrev

<400> SEQUENCE: 16
tttttttctt aagttagcag tgaatggtcc gg                                     32
```

HUMAN-DERIVED RECOMBINANT FSH FOR CONTROLLED OVARIAN STIMULATION

The present invention relates to compositions and pharmaceutical products for the treatment of infertility.

Assisted reproductive technology (ART) techniques such as in vitro fertilisation (IVF) are well known. These ART techniques generally require a step of controlled ovarian stimulation (COS), in which a cohort of follicles is stimulated to full maturity. Standard COS regimens include administration of gonadotrophins, such as follicle stimulating hormone (FSH) alone or in combination with luteinising hormone (LH) activity to stimulate follicular development, normally with administration of a GnRH analogue prior to and/or during stimulation to prevent premature LH surge. The pharmaceutical compositions generally used for COS include recombinant follicle stimulating hormone (rFSH), urinary derived FSH, recombinant FSH+LH preparations, urinary derived menotrophin [human menopausal gonadotrophin (hMG)] and highly purified human menopausal gonadotrophin (HP-hMG). IVF can be associated with a risk of ovarian hyperstimulation syndrome (OHSS), which can be life threatening in severe cases.

The ability to predict the response potential of women to controlled ovarian stimulation (COS) may allow the development of individualised COS protocols. This could, for example, reduce the risk of OHSS in women predicted to have an excessive response to stimulation, and/or improve pregnancy outcomes in women classed as poor responders. The serum concentration of anti-Müllerian hormone (AMH) is now established as a reliable marker of ovarian reserve. Decreasing levels of AMH are correlated with reduced ovarian response to gonadotrophins during COS. Further, high levels of AMH are a good predictor of excessive ovarian response, and an indicator of risk of OHSS.

In a preliminary study of women under 35 years old undergoing ART, the CONSORT dosing algorithm (incorporating basal FSH, BMI, age and AFC) was used to predict the optimal FSH starting dose for COS in women at risk of developing OHSS (Olivennes et. al., 2009). Individualising the dose did lead to adequate oocyte yield and good pregnancy rate. However, there were high rates of cancellations in the low dose group (75 IU FSH) due to inadequate response, and OHSS did occur in a significant proportion of the patients.

There is therefore a need for a composition for use in individualised COS protocols which provides adequate response to stimulation, and/or decreased risk of OHSS.

As indicated above, standard COS protocols may include administration of FSH. FSH is naturally secreted by the anterior pituitary gland and functions to support follicular development and ovulation. FSH comprises a 92 amino acid alpha sub-unit, also common to the other glycoprotein hormones LH and CG, and a 111 amino acid beta sub-unit unique to FSH that confers the biological specificity of the hormone (Pierce and Parsons, 1981). Each sub-unit is post translationally modified by the addition of complex carbohydrate residues. Both subunits carry 2 sites for N-linked glycan attachment, the alpha sub-unit at amino acids 52 and 78 and the beta sub-unit at amino acid residues 7 and 24 (Rathnam and Saxena, 1975, Saxena and Rathnam, 1976). FSH is thus glycosylated to about 30% by mass (Dias and Van Roey. 2001. Fox et al. 2001).

FSH purified from post-menopausal human urine has been used for many years in infertility treatment; both to promote ovulation in natural reproduction and to provide oocytes for assisted reproduction technologies. The currently approved recombinant FSH (rFSH) products for ovarian stimulation, such as follitropin alfa (GONAL-F, Merck Serono/EMD Serono) and follitropin beta (PUREGON/FOLLISTIM, MSD/Schering-Plough), are derived from a Chinese Hamster Ovary (CHO) cell line. Currently, no rFSH products from a human cell line are commercially available.

There is considerable heterogeneity associated with FSH preparations which relates to differences in the amounts of various isoforms present. Individual FSH isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural FSH is highly complex. The glycans in naturally derived pituitary FSH can contain a wide range of structures that can include combinations of mono-, bi-, tri- and tetra-antennary glycans (Pierce and Parsons, 1981. Ryan et al., 1987. Baenziger and Green, 1988). The glycans can carry further modifications: core fucosylation, bisecting glucosamine, chains extended with acetyl lactosamine, partial or complete sialylation, sialylation with $\alpha 2,3$ and $\alpha 2,6$ linkages, and sulphated galactosamine substituted for galactose (Dalpathado et al., 2006). Furthermore, there are differences between the distributions of glycan structures at the individual glycosylation sites. A comparable level of glycan complexity has been found in FSH derived from the serum of individuals and from the urine of post-menopausal women (Wide et al., 2007).

The glycosylation of recombinant FSH products reflects the range of glycosyl-transferases present in the host cell line. The commercially available rFSH products are derived from engineered Chinese hamster ovary cells (CHO cells). The range of glycan modifications in CHO cell derived rFSH are more limited than those found on the natural products. Examples of the reduced glycan heterogeneity found in CHO cell derived rFSH include a lack of bisecting glucosamine and a reduced content of core fucosylation and acetyl lactosamine extensions (Hard et al., 1990). In addition, CHO cells are only able to add sialic acid using the $\alpha 2,3$ linkage (Kagawa et al, 1988, Takeuchi et al, 1988, Svensson et al., 1990); CHO cell derived rFSH only includes $\alpha 2,3$-linked sialic acid and does not include $\alpha 2,6$-linked sialic acid.

Thus CHO cell derived FSH is different from naturally produced FSH (e.g. human Pituitary/serum/urinary FSH) which contains glycans with a mixture of $\alpha 2,3$ and $\alpha 2,6$-linked sialic acid, with a predominance of the former.

Further, it has also been demonstrated that the commercially available recombinant FSH preparation differs in the amounts of FSH with an isoelectric point (pi) of below 4 (considered the acidic isoforms) when compared to pituitary, serum or post-menopausal urine FSH (Ulloa-Aguirre et al. 1995). The amount of acidic isoforms in the urinary preparations was much higher as compared to the CHO cell derived recombinant products, Gonal-f (Merck Serono) and Puregon (Schering Plough) (Andersen et al. 2004). This must reflect a lower molar content of sialic acid in the recombinant FSH since the content of negatively-charged glycan modified with sulphate is low in recombinant FSH. The lower sialic acid content, compared to natural FSH, is a feature of both commercially available recombinant FSH products and may reflect a limitation in the manufacturing process.

The circulatory life-time of FSH has been documented for materials from a variety of sources. Some of these materials have been fractionated on the basis of overall molecular charge, as characterised by their pI, in which more acid equates to a higher negative charge. As previously stated the major contributor to overall molecular charge is the total sialic content of each FSH molecule. For instance, rFSH (Organon) has a sialic acid content of around 8 mol/mol, whereas urine-derived FSH has a higher sialic acid content (de Leeuw et al. 1996). The corresponding plasma clearance rates in the rat are 0.34 and 0.14 ml/min (Ulloa-Aguirre et al. 2003). In another example where a sample of recombinant FSH was split into high and low pI fractions, the in vivo potency of the high pI (lower sialic acid content) fraction was decreased and it had a shorter plasma half-life (D'Antonio et al. 1999). It has also been reported that the more basic FSH circulating during the later stages of the ovulation cycle is due to the down-regulation of α2,3 sialyl-transferase in the anterior pituitary which is caused by increasing levels of estradiol (Damian-Matsumara et al. 1999. Ulloa-Aguirre et al. 2001). Results for the α2,6 sialyl-transferase have not been reported.

Thus, as set out above, recombinant proteins expressed using the CHO system will differ from their natural counterparts in their type of terminal sialic acid linkages. This is an important consideration in the production of biologicals for pharmaceutical use since the carbohydrate moieties may contribute to the pharmacological attributes of the molecule.

The present applicants have developed a human derived recombinant FSH which is the subject of International Patent Application No. PCT/GB2009/000978, published as WO2009/127826A. Recombinant FSH with a mixture of both α2,3 and α2,6-linked sialic acid was made by engineering a human cell line to express both rFSH and α2,3 sialyltransferase. The expressed product is highly acidic and carries a mix of both α2,3- and α2,6-linked sialic acids; the latter provided by the endogenous sialyl transferase activity. It was found that the type of sialic acid linkage, α2,3- or α2,6-, can have a dramatic influence on biological clearance of FSH. Recombinant FSH with a mixture of both α2,3 and α2,6-linked sialic acid has two advantages over rFSH expressed in conventional CHO cells: first the material is more highly sialylated due to the combined activities of the two sialyltransferases; and secondly the material more closely resembles the natural FSH. This is likely to be more biologically appropriate compared to CHO cell derived recombinant products that have produce only α2,3 linked sialic acid (Kagawa et al, 1988, Takeuchi et al, 1988, Svensson et al., 1990) and have decreased sialic acid content (Ulloa-Aguirre et al. 1995., Andersen et al. 2004).

The rFSH product disclosed in International Patent Application No. PCT/GB2009/000978 contains branched glycan moieties. FSH comprises glycans (attached to the FSH glycoproteins) and these glycans may contain a wide variety of structures. As is well known in the art, branching (of a glycan) can occur with the result that the glycan may have 1, 2, 3, 4 or more terminal sugar residues or "antennae"; glycans with 1, 2, 3 or 4 terminal sugar residues or "antennae" are referred to respectively as mono-antennary, di-antennary, tri-antennary or tetra-antennary structures. Glycans may have sialylation presence on mono-antennary and/or di-antennary and/or tri-antennary and/or tetra-antennary structures. An example rFSH disclosed in International Patent Application No. PCT/GB2009/000978 included mono-sialylated, di-sialylated, tri-sialylated and tetra-sialylated glycan structures with relative amounts as follows: 9-15% mono-sialylated; 27-30% di-sialylated; 30-36% tri-sialylated and 25-29% tetra-sialylated. As is well known, a mono-sialylated glycan structure carries one sialic acid residue; a di-sialylated glycan structure carries two sialic acid residues; a tri-sialylated glycan structure carries three sialic acid residues; and a tetra-sialylated glycan structure carries four sialic acid residues. Herein, terminology such as "X % mono-sialylated", "X % di-sialylated", "X % tri-sialylated" or "X % tetra-sialylated" refers to the number of glycan structures on FSH which are mono-, di, tri or tetra sialylated (respectively), expressed as a percentage (X %) of the total number of glycan structures on the FSH which are sialylated in any way (carry sialic acid). Thus, the phrase "30-36% tri-sialylated glycan structures" means that, of the total number of glycan structures on the FSH which carry sialic acid residues (that is, are sialylated), 30 to 36% of these glycan structures are tri sialylated (carry three sialic acid residues). The applicants have surprisingly found that FSH having a specific amount of tetra-sialylated glycan structures (which is different to that of the example rFSH product disclosed in PCT/GB2009/000978 mentioned above) is markedly more potent then recombinant FSH products which are currently on the market. The amino acid sequence of the applicant's products is the native sequence and is identical to natural human FSH and existing CHO-derived rFSH products. However, the present applicants have found that human derived recombinant FSH products (i.e. recombinant FSH produced or expressed in a human cell line e.g. made by engineering a human cell line) which have a mixture of both α2,3 and α2,6-linked sialic acid and/or a specific amount of tetra-sialylated glycan structures may be particularly effective when utilised in (e.g. individualised) COS protocols.

According to the present invention in a first aspect there is provided a product (e.g. a pharmaceutical composition) comprising follicle stimulating hormone (FSH) for use in the treatment of infertility in a patient (e.g. a patient having serum AMH level of 0.05 pmol/L or above, for example 0.5 pmol/L or above), wherein the product comprises a dose of, or a dose equivalent to, 1-24 μg, for example 2-24 μg, for example 2 to 15 μg, human derived recombinant FSH. Preferably the product comprises a dose of, or a dose equivalent to, 4.5 to 12.5 μg, for example 5 to 12.5 μg, for example 6 to 12.5 μg, for example 6.3 to 10.5 μg, human derived recombinant FSH.

According to the invention there is provided a product (e.g. a pharmaceutical composition) comprising follicle stimulating hormone (FSH) for use in the treatment of infertility in a patient having serum AMH level of <15 pmol/L (e.g. 0.05 pmol/L to 14.9 pmol/L), wherein the product comprises a (e.g. daily) dose of, or dose equivalent to, 9 to 14 μg, for example 11 to 13 μg, for example 12 μg human derived recombinant FSH. Preferably the FSH is a recombinant FSH ("rFSH" or "recFSH"). Preferably the FSH is a human cell line derived recombinant FSH. The dose provides an effective response while minimising risk of OHSS. Preferably the treatment of infertility comprising a step of determining (e.g. measuring) the serum AMH level of the patient, and administering the dose to a patient having serum AMH level of <15 pmol/L (e.g. 0.05 pmol/L to 14.9 pmol/L).

According to the invention in a further aspect there is provided a product (e.g. a pharmaceutical composition) comprising follicle stimulating hormone (FSH) for use in the treatment of infertility in a patient having serum AMH level of ≥15 pmol/L, wherein the product comprises a (e.g. daily) dose of, or dose equivalent to, 5 to 12.5 μg, for example 6 to 10.5 μg human derived recombinant FSH. Preferably the FSH is a recombinant FSH ("rFSH" or "recFSH"). Preferably the FSH is a human cell line derived recombinant FSH. The dose provides an effective response while minimising risk of OHSS. Preferably the treatment of infertility comprising a step of determining (e.g. measuring) the serum AMH level of the patient, and administering the dose to a patient having serum AMH level of ≥15 pmol/L. In one embodiment, the product is for use in the treatment of infertility in a patient having serum AMH level of 15 to 24.9 pmol/L, and the product is for administration at a (e.g. daily) dose of, or dose equivalent to, 5 to 12 µg, for example 7 to 12 µg, for example 8.7 to 10 µg, human derived recombinant FSH (preferably 9 to 10 µg human derived recombinant FSH) In this embodiment, the treatment of infertility may comprise a step of determining (e.g. measuring) the serum AMH level of the patient, and administering the dose to a patient having serum AMH level of 15 to 24.9 pmol/L. In another embodiment, the product is for use in the treatment of infertility in a patient having serum AMH level of 25 to 34.9 pmol/L, and the product is for administration at a (e.g. daily) dose of, or dose equivalent to, 5 to 12 µg, for example 6 to 9 µg, for example 7 to 8 µghuman derived recombinant FSH (preferably 7.3 to 8 µg human derived recombinant FSH). In this embodiment, the treatment of infertility may comprise a step of determining (e.g. measuring) the serum AMH level of the patient, and administering the dose to a patient having serum AMH level of 25 to 34.9 pmol/L. In another embodiment, the product is for use in the treatment of infertility in a patient having serum AMH level of ≥35 pmol/L, and the product is for administration at a (e.g. daily) dose of, or dose equivalent to, 5 to 11 µg, for example 6.3 to 7 µg, human derived recombinant FSH (preferably 6 to 7 µg human derived recombinant FSH). In this embodiment, the treatment of infertility may comprise a step of determining (e.g. measuring) the serum AMH level of the patient, and administering the dose to a patient having serum AMH level of ≥35 pmol/L.

The doses above may be for treatment of infertility in the patient's (subject's) first stimulation protocol. It will be appreciated that for further stimulation cycles, the doses may be adjusted according to actual ovarian response in the first cycle.

The applicants have found that it is generally necessary to retrieve in the region of nine oocytes in order to enable selection of two high quality oocytes for transfer.

The applicants have found that for subjects having low AMH (AMH <15 pmol/L per litre) a reasonably high dose of recombinant FSH is required (for example 12 µg) to achieve this. At this dose, 8 to 14 oocytes will be retrieved from 60% of subjects with low AMH. This is an unexpected and significant improvement over treatment of subjects with low AMH treated with 150 IU Gonal-f, where 8 to 14 oocytes are retrieved from only 33% of subjects. The applicants have found that there is no need to adjust this dose according to the bodyweight of the patient.

However, 60% of the population (and 80% of women under 30 treated for infertility) have high AMH (that is, AMH of ≥15 pmol/L). For these subjects it is generally fairly straightforward to retrieve a mean of 9 to 11 oocytes; the problem with stimulation protocols is the risk of OHSS. The applicants have found that in patients dosed at low doses of human recombinant FSH that there is a relationship between oocytes retrieved and body weight of the subject. This means that there may be a risk associated with treatment with a fixed dose of FSH (which is usual in the art). The present applicants have established a relationship between dose of FSH and AMH level and weight of the subject which provides an improved safety profile (reduced risk of OHSS) with acceptable or improved oocyte retrieval compared to the known treatment protocols (see example 10).

According to the invention in a further aspect there is provided a product (e.g. a pharmaceutical composition) comprising follicle stimulating hormone (FSH) for use in the treatment of infertility in a patient having serum AMH level of ≥15 pmol/L, wherein the product is for administration at a (e.g. daily) dose of, or dose equivalent to, 0.09 to 0.19 µg (for example 0.09 to 0.17 µg) human derived recombinant FSH per kg bodyweight of the patient. Preferably the treatment of infertility comprises a step of determining (e.g. measuring) the serum AMH level of the patient, and administering the dose to a patient having serum AMH level of ≥15 pmol/L. In one embodiment, the product is for use in the treatment of infertility in a patient having serum AMH level of 15 to 24.9 pmol/L, and the product is for administration at a (e.g. daily) dose of, or dose equivalent to, 0.14 to 0.19 µg human derived recombinant FSH (preferably 0.15 to 0.16 µg human derived recombinant FSH) per kg bodyweight of the patient. In this embodiment, the treatment of infertility may comprise a step of determining (e.g. measuring) the serum AMH level of the patient, and administering the dose to a patient having serum AMH level of 15 to 24.9 pmol/L. In another embodiment, the product is for use in the treatment of infertility in a patient having serum AMH level of 25 to 34.9 pmol/L, and the product is for administration at a (e.g. daily) dose of, or dose equivalent to, 0.11 to 0.14 µg human derived recombinant FSH (preferably 0.12 to 0.13 µg human derived recombinant FSH) per kg bodyweight of the patient. In this embodiment, the treatment of infertility may comprise a step of determining (e.g. measuring) the serum AMH level of the patient, and administering the dose to a patient having serum AMH level of 25 to 34.9 pmol/L. In a still further embodiment, the product is for use in the treatment of infertility in a patient having serum AMH level of ≥35 pmol/L, and the product is for administration at a (e.g. daily) dose of, or dose equivalent to, 0.10 to 0.11 µg human derived recombinant FSH per kg bodyweight of the patient. In this embodiment, the treatment of infertility may comprise a step of determining (e.g. measuring) the serum AMH level of the patient, and administering the dose to a patient having serum AMH level of ≥35 pmol/L. Preferably the FSH is a recombinant FSH ("rFSH" or "recFSH"). Preferably the FSH is a human cell line derived recombinant FSH. The doses provide an effective response while minimising risk of OHSS.

The doses above may be for treatment of infertility in the patient's (subject's) first stimulation protocol. It will be appreciated that for further stimulation cycles, the doses may be adjusted according to actual ovarian response in the first cycle.

According to the invention in a still further aspect there is provided a product (e.g. a pharmaceutical composition) comprising follicle stimulating hormone (FSH) for use in the treatment of infertility in a patient having serum AMH level of <15 pmol/L, wherein the product is for administration at a (e.g. daily) dose of, or dose equivalent to, 0.15 to 0.21 µg, (for example 0.19 to 0.21 µg) human derived recombinant FSH per kg bodyweight of the patient. Preferably the treatment of infertility comprises a step of determining (e.g. measuring) the serum AMH level of the patient, and administering the dose to a patient having serum AMH level of <15 pmol/L. However, it is not required that patients having serum AMH level of <15 pmol/L are dosed by body weight. It will be appreciated that these doses may be readily converted to treat patients with dosing according to their BMI, using conversions well known in the art.

The product (e.g. pharmaceutical compostion) may be for use in the treatment of infertility in a patient having serum AMH of 5.0-14.9 pmol/L, wherein the product comprises a dose of, or dose equivalent to, 6 to 18 µg, for example 8 to 11 µg, for example 8.5 to 10.2 µg human derived recombinant FSH. The product may be for use in the treatment of infertility in a patient having serum AMH 15.0-29.9 pmol/L, wherein the product comprises a dose of, or a dose equivalent to, 4.8 to 15 µg, for example 6 to 9 µg, for example 6.8 to 8.5 µg human derived recombinant FSH. The product may be for use in the treatment of infertility in a patient having serum AMH 30-44.9 pmol/L, wherein the product comprises a dose of, or a dose equivalent to, 3.6 to 12 µg, for example 4 to 7 µg, for example 5.1 to 6.8 µg human derived recombinant FSH. The product may be for use in the treatment of infertility in a patient having serum AMH 45 pmol/L or greater, wherein the product comprises a dose of, or a dose equivalent to, 2 to 9 µg, for example 2.4 to 9 µg (for example 3.4 to 5.1 µg) or 2 to 5 µg human derived recombinant FSH. The product may comprise follicle stimulating hormone (FSH) for use in the treatment of infertility in a patient having serum AMH of 5 pmol/L or less, wherein the product comprises a dose of, or a dose equivalent to 7.2 to 24 µg, for example 10 to 15 µg for example 10.2 to 13.6 µg, human derived recombinant FSH. The product may be for use in the treatment of infertility in a patient wherein the product comprises a dose of, or dose equivalent to, 4.8 to 18 µg, for example 6 to 11 µg, for example 6.8 to 10.2 µg human derived recombinant FSH. Preferably the FSH is a recombinant FSH ("rFSH" or "recFSH"). Preferably the FSH is a human cell line derived recombinant FSH.

Preferably the rFSH (e.g. human cell line derived recombinant FSH) includes α2,3- and α2,6-sialylation. The FSH (rFSH) for use according to the invention may have 1% to 99% of the total sialylation being α2,3-sialylation. The FSH (rFSH) according to the invention may have 1% to 99% of the total sialylation being α2,6-sialylation. Preferably, 50 to 70%, for example 60 to 69%, for example about 65%, of the total sialylation is α2,3-sialylation. Preferably 25 to 50%, for example 30 to 50%, for example 31 to 38%, for example about 35%, of the total sialylation is α2,6-sialylation.

Preferably the rFSH (e.g. human cell line derived recombinant FSH) includes mono-, di-, tri- and tetra-sialylated glycan structures, wherein 15-24%, for example 17-23% of the sialylated glycan structures are tetrasialylated glycan structures (e.g. as shown by WAX analysis of charged glycans, as set out in the Examples below). The FSH comprises glycans (attached to the FSH glycoproteins). It is well known that glycans in FSH may contain a wide variety of structures. These may include combinations of mono, bi, tri and tetra-antennary glycans. Herein, terminology such as "X % of the sialylated glycan structures are tetrasialylated glycan structures" refers to the number of glycan structures on the FSH which are tetra sialylated, i.e. carry four sialic acid residues, expressed as a percentage (X %) of the total number of glycan structures on the FSH which are sialylated in any way (carry sialic acid). Thus, the phrase "15-24% of the sialylated glycan structures are tetrasialylated glycan structures" means that, of the total number of glycan structures on FSH which carry sialic acid residues (that is, are sialylated), 15 to 24% of these glycan structures are tetra sialylated (carry four sialic acid residues).

The rFSH may be present as a single isoform or as a mixture of isoforms.

The applicants have devised "individualised" COS protocols wherein specific doses of recombinant FSH having specific characteristics are used to treat patients based on their specific AMH levels, thereby increasing the likelihood of adequate response to stimulation (e.g. in patients having a low response potential), and/or decreased risk of OHSS (e.g. in patients classed as high or excessive responders).

The serum level of AMH may be determined (e.g. measured) by any method known in the art. Preferably the serum AMH level is measured using the AMH Gen-II enzyme linked immunosorbent assay, a kit (Beckman Coulter, Inc., Webster, Texas). This assay can detect can detect AMH concentrations greater than 0.57 pmol/L with a minimum limit of quantitation of 1.1 pmol/L. Other assays may be used.

Herein, serum AMH values are generally recited in terms of pmol/L. This may be converted to ng/mL using the conversion equation 1 ng/ml AMH=7.1 pmol/L AMH.

Herein the terms "patient" and "subject" are used interchangeably.

The product (e.g. pharmaceutical composition) preferably comprises a daily dose of, or a daily dose equivalent to, the amounts of human derived rFSH defined above, herein, and in the claims. The (daily) dose may be an initial dose (i.e. it may be reduced, increased, or maintained during the treatment).

The product (e.g. pharmaceutical composition) may be for (daily) administration of FSH starting on day one of treatment and continuing for seven to thirteen days, for example nine to thirteen days, for example 10 to 13 days, for example 10 to 11 days. The product (e.g. pharmaceutical composition) may be for administration 12 to 16, e.g. 13 to 15, e.g. 14 days after administration of (e.g. after initiation of administration of, e.g. after initiation of daily administration of) a GnRH agonist (e.g. Synarel, Lupron, Decapeptyl). The product (e.g. pharmaceutical composition) may be for administration with a GnRH agonist. The product (e.g. pharmaceutical composition) may be for administration prior to administration of a GnRH antagonist (e.g. ganirelix, cetrorelix), for example for administration five or six days prior to administration of a GnRH antagonist. The product (e.g. pharmaceutical composition) may be for administration with a GnRH antagonist. Preferably the product (e.g. pharmaceutical composition) is for administration prior to administration of a high (ovulatory) dose of hCG (for example 4,000 to 11,000 IU hCG, e.g. 5,000 IU hCG, 10,000 IU hCG etc.; or 150 to 350 microgram recombinant hCG, for example 250 microgram recombinant hCG) to induce final follicular maturation.

It will be appreciated that the product may be for dosing at frequencies more (or less) than daily, in which case the relevant doses will be equivalent to the (daily) doses specified herein.

Herein the term "treatment of infertility" includes treatment of infertility by controlled ovarian stimulation (COS) or methods which include a step or stage of controlled ovarian stimulation (COS), for example Intra Uterine Insemination (IUI), in vitro fertilisation (IVF), or intracytoplasmic sperm injection (ICSI). The term "treatment of infertility" includes treatment of infertility by ovulation induction (OI) or by methods which include a step or stage of ovulation induction (OI). The term "treatment of infertility" includes treatment of infertility in a subject having tubal or unexplained infertility, including treatment of infertility in a subject having endometriosis, for example stage I or stage II endometriosis, and/or in a subject having anovulatory infertility, for example WHO type II anovulatory infertility, and/or in a subject with a partner with male factor infertility. The product (or composition) may be for (use in) the treatment of infertility (and/or for controlled ovarian stimulation) in a subject having endometriosis, for example in a subject having stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil Steril 1997; 67,817 821.].

The product (composition) may be for (use in) the treatment of infertility (and/or for controlled ovarian stimulation) in a subject having normal serum FSH level of 1 to 16 IU/L, for example 1 to 12 IU/L, in the early follicular phase.

The product (composition) may be for (use in) the treatment of infertility (and/or for controlled ovarian stimulation) in a subject aged 18 to 42 years, for example 25 to 37 years. The product may be for (use in) the treatment of infertility (and/or for controlled ovarian stimulation) in a subject having BMI >1 and BMI <35 kg/m$^2$, for example a subject having BMI >18 and BMI <25 kg/m$^2$, for example a subject having BMI >20 and BMI <25 kg/m$^2$.

The rFSH may preferably include 27-33%, for example 30-32%, tri-sialylated glycan structures. The rFSH may preferably include 24-33%, for example 26-30%, di-sialylated glycan structures. The rFSH may preferably include 12-21%, for example 15-17%, mono-sialylated glycan structures. The rFSH preferably includes mono-sialylated, di-sialylated, tri-sialylated and tetra-sialylated glycan structures with relative amounts as follows: 15 to 17% mono-sialylated; 26-30% di-sialylated; 27-33% (e.g. 29 to 32%, e.g 30-32%, e.g 30 to 31%) tri-sialylated and 17-23% tetra-sialylated (e.g. as shown by WAX analysis of charged glycans, as set out in the Examples). The rFSH may include from 0 to 7%, for example 0.1 to 7%, for example 3 to 6%, for example 5 to 6%, neutral sialylated structures. The FSH comprises glycans (attached to the FSH glycoproteins). Herein, terminology such as "X % mono-sialylated", "X % di-sialylated", "X % tri-sialylated" or "X % tetra-sialylated" refers to the number of glycan structures on FSH which are mono-, di, tri or tetra sialylated (respectively), expressed as a percentage (X %) of the total number of glycan structures on the FSH which are sialylated in any way (carry sialic acid). Thus, the phrase "27-33% tri-sialylated glycan structures" means that, of the total number of glycan structures on FSH which carry sialic acid residues (that is, are sialylated), 27 to 33% of these glycan structures are tri sialylated (carry three sialic acid residues).

The rFSH may have a sialic acid content [expressed in terms of a ratio of moles of sialic acid to moles of protein] of 6 mol/mol or greater, for example between 6 mol/mol and 15 mol/mol, e.g between 8 mol/mol and 14 mol/mol, for example between 10 mol/mol and 14 mol/mol, e.g between 11 mol/mol and 14 mol/mol, e.g between 12 mol/mol and 14 mol/mol, e.g. between 12 mol/mol and 13 mol/mol. The rFSH may be produced or expressed in a human cell line.

The FSH (rFSH) for use according to the invention may have 1% to 99% of the total sialylation being α2,3-sialylation. The rFSH may have 10% or more of the total sialylation being α2,3-sialylation. For example, 20, 30, 40, 50, 60, 70, 80 or 90% or more of the total sialylation may be α2,3-sialylation. The rFSH may preferably include α2,3-sialylation in an amount which is from 50 to 70% of the total sialylation, for example from 60 to 69% of the total sialylation, for example from 63 to 67%, for example around 65% of the total sialylation. The FSH (rFSH) for use according to the invention may have 1% to 99% of the total sialylation being α2,6-sialylation. The rFSH (or rFSH preparation) of the invention may have 5% or more, for example 5% to 99%, of the total sialylation being α2,6-sialylation. The rFSH may have 50% or less of the total sialylation being α2,6-sialylation. The rFSH may preferably include α2,6-sialylation in an amount which is from 25 to 50% of the total sialylation, for example from 30 to 50% of the total sialylation, for example from 31 to 38%, for example around 35% of the total sialylation. By sialylation it is meant the amount of sialic residues present on the FSH carbohydrate structures. α2,3-sialylation means sialylation at the 2,3 position (as is well known in the art) and α2,6 sialylation at the 2,6 position (also well known in the art). Thus "% of the total sialylation may be α 2,3 sialylation" refers to the % of the total number of sialic acid residues present in the FSH which are sialylated in the 2,3 position. The term "% of the total sialylation being α2,6-sialylation" refers to the % of the total number of sialic acid residues present in the FSH which are sialylated in the 2,6 position.

The rFSH may have a sialic acid content (amount of sialylation per FSH molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

The rFSH may be rFSH or a rFSH preparation in which 16% or fewer (e.g. 0.1 to 16%) of the glycans comprise (e.g. carry) bisecting N-acetylglucosamine (bisecting GlcNAc or bisGlcNAc). Preferably the rFSH (or rFSH preparation) is an rFSH or rFSH preparation in which 8 to 14.5% of the glycans comprise (e.g. carry) a bisecting N-acetylglucosamine (bisecting GlcNAc or bisGlcNAc).

It will be understood that FSH comprises glycans attached to the FSH glycoproteins. It will also be understood that 100% of the glycans refers to or means all of the glycans attached to the FSH glycoproteins. Thus, herein, the terminology "8 to 14.5% of the glycans comprise (carry) bisecting N-acetylglucosamine" means that 8 to 14.5% of the total number of glycans attached to the FSH glycoproteins include/carry bisecting N-acetylglucosamine; "16% or fewer of the glycans comprise (carry) bisecting N-acetylglucosamine" means that 16% or fewer of the total number of glycans attached to the FSH glycoproteins include/carry bisecting N-acetylglucosamine, and so on.

The applicants have found that recombinant FSH (rFSH preparations; rFSH compositions) in which 16% or fewer (e.g. 8 to 14.5%) of the glycans comprised in the FSH glycoproteins carry bisecting GlcNac may have advantageous pharmacokinetic properties. It is believed the advantageous properties may arise because the amount of glycans which carry bisecting GlcNac is similar to that in the human urinary derived product Bravelle, which is rather less than that of other recombinant FSH preparations such as those disclosed in WO2012/017058.

The rFSH (or rFSH preparation) may be an rFSH or rFSH preparation in which 20% or more of the glycans comprise (e.g. carry) N-Acetylgalactosamine (GalNAc), for example in which 20% or more of the glycans comprise (e.g. carry) a terminal GalNAc. Preferably the rFSH (or rFSH preparation) is an FSH or FSH preparation in which the 40 to 55%, for example 42% to 52%, of the glycans comprise (e.g. carry) GalNAc. Preferably the rFSH (or rFSH preparation) is an FSH or FSH preparation in which the 40 to 55%, for example 42% to 52%, of the glycans comprise (e.g. carry) terminal GalNAc.

It will be understood that FSH comprises glycans attached to the FSH glycoproteins. It will also be understood that 100% of the glycans refers to or means all of the glycans attached to the FSH glycoproteins. Thus, herein, the terminology "wherein 20% or more of the glycans comprise (e.g. carry) GalNAc" means that 20% or more of the total number of glycans attached to the FSH glycoproteins include/carry N-Acetylgalactosamine (GalNAc); "40 to 55%, for example 42% to 52%, of the glycans comprise (e.g. carry) terminal GalNAc" means that 40 to 55%, for example 42% to 52%, of the total number of glycans attached to the FSH glycoproteins include/carry terminal GalNAc, and so on.

It appears that the availability of the α2,6-linkage increases the number of tetra sialylated structures, compared to CHO cell derived products which have only the α2,3-linkage available. The applicants have also found that their rFSH is distinguished over other approved products because of the sugar composition: it includes, or may include, a specific amount of GalNac. This may be linked to tetrasialylation and potency because the 2,6-sialylation is associated with GalNac. In other words, the present applicants have developed an rFSH product which includes specific characteristics (2,6-linker sites, GalNac) which provide rFSH with high degree of sialylation, which appears to lead to improved potency in vivo.

The rFSH (or rFSH preparation) may have 16 to 24% of the glycans comprising (e.g. terminal) 1 fucose-lewis, for example 16.5 to 18% of the glycans comprising (e.g. terminal) 1 fucose-lewis. The rFSH (or rFSH preparation) may have 1.5 to 4.5%, for example 2 to 4%, for example 3.7%, of the glycans comprising (e.g. terminal) 2 fucose -lewis. The content of fucose-lewis may have an effect on potency.

The rFSH may be produced or expressed in a human cell line, for example a Per.C6 cell line, a HEK293 cell line, a HT1080 cell line etc. This may simplify (and render more efficient) the production method because manipulation and control of e.g. the cell growth medium to retain sialylation may be less critical than with known processes. The method may also be more efficient because there is little basic rFSH produced compared to production of known rFSH products; more acidic rFSH is produced and separation/removal of basic FSH is less problematic. The rFSH may be produced or expressed in a PER.C6® cell line, a PER.C6® derived cell line or a modified PER.C6® cell line. rFSH which is produced or expressed in a human cell line (e.g. PER.C6® cell line, HEK293 cell line, HT1080 cell line etc.) will include some α2,6-linked sialic acids (α2,6 sialylation) provided by endogenous sialyl transferase activity [of the cell line] and will include some α2,3-linked sialic acids (α2,3 sialylation) provided by endogenous sialyl transferase activity. The cell line may be modified using α2,3-sialyltransferase. The cell line may be modified using α2,6-sialyltransferase. Alternatively or additionally, the rFSH may include α2,6-linked sialic acids (α2,6 sialylation) provided by endogenous sialyl transferase activity [of the cell line]. Herein, the term "human derived recombinant FSH" means recombinant FSH which is produced or expressed in a human cell line (e.g. recombinant FSH made by engineering a human cell line).

The rFSH may be produced using α2,3- and/or α2,6-sialyltransferase. In an example, rFSH is produced using α2,3-sialyltransferase. The rFSH may include α2,6-linked sialic acids (α2,6 sialylation) provided by endogenous sialyl transferase activity. The product may be a pharmaceutical composition. The pharmaceutical composition is for the treatment of infertility. The treatment of infertility may comprise assisted reproductive technologies (ART), ovulation induction or intrauterine insemination (IUI). The pharmaceutical composition may be used, for example, in medical indications where known FSH preparations are used.

The product or composition can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectible organic esters such as ethyl oleate. The compositions of the present invention also can contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like. The product or composition may further comprise a salt comprising a pharmaceutically acceptable alkali metal cation selected from the group consisting of $Na^+$- or $K^+$-salts, or a combination thereof. Preferably the salt is a $Na^+$-salt, for example NaCl or $Na_2SO_4$.

Preferably the product or composition comprises recombinant FSH and one or more of Polysorbate 20, L-methionine, phenol, disodium sulphate and sodium phosphate buffer.

In some cases, to effect prolonged action it is desirable to slow the absorption of FSH (and other active ingredients, if present) from subcutaneous or intramuscular injection. This can be accomplished by the use of a liquid suspension of crystalline or amorphous material with poor water solubility. The rate of absorption of FSH then depends upon its rate of dissolution which, in turn, can depend upon crystal size and crystalline form. Alternatively, delayed absorption of a parenterally administered FSH combination form is accomplished by dissolving or suspending the FSH combination in an oil vehicle. Injectable depot forms can be made by forming microencapsule matrices of the FSH (and other agents, if present) in biodegradable polymers such as polylactide-polyglycolide. Depending upon the ratio of FSH to polymer and the nature of the particular polymer employed, the rate of FSH release can be controlled. Examples of other biodegradable polymers include polyvinylpyrrolidone, poly (orthoesters), poly(anhydrides) etc. Depot injectable formulations are also prepared by entrapping the FSH in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

The product or composition may be formulated for single use or for multiple use (multiple dose). If the product or composition is formulated for multiple use, it is preferred that a preservative is included. If a preservative is included, benzyl alcohol, phenol and/or m-cresol are preferred; however, the preservative is by no means limited to these examples. The single use or multiple use formulated product or composition may further comprise a salt comprising a pharmaceutically acceptable alkali metal cation selected from the group consisting of $Na^+$- or $K^+$-salts, or a combination thereof. Preferably the salt is a $Na^+$-salt, for example NaCl or $Na_2SO_4$.

The product or composition may be included in a container such as a vial, prefilled cartridge (e.g. for single administration or multiple use) or an injection device such as a "pen" for e.g. administration of multiple doses.

The product or composition may be a formulation (e.g. injectable formulation) including FSH (optionally with hCG, LH, LH activity etc.) The LH activity, if present, may originate from LH or human chorionic gonadotropin, hCG. If there is more than one active ingredient (i.e. FSH and e.g. hCG or LH) these may be suitable for administration separately or together. If administered separately, administration can be sequential. The product can be supplied in any appropriate package. For example, a product can include a number of containers (e.g. pre-filled syringes or vials) containing either FSH or hCG, or a combination (or combination) of both FSH and hCG. The hCG may be recombinant hCG or urinary hCG. If the product includes a number of containers (e.g. pre-filled syringes or vials) containing FSH, e.g. recombinant FSH, each container may include the same amount of FSH. One or more containers may include different amounts of FSH. The syringes or vials may be packaged in a blister package or other means to maintain sterility. Any product can optionally contain instructions for using the FSH (and e.g. hCG if present) formulations. The pH and exact concentration of the various components of the pharmaceutical composition are adjusted in accordance with routine practice in this field. See GOODMAflII and GILMAN's THE PHARMACOLOGICAL BASIS FOR THERAPEUTICES, $7^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

According to the present invention in a further aspect there is provided a method of treatment of infertility comprising: (a) measuring the serum AMH level of a subject; and (b) administration to the subject a dose of, or a dose equivalent to, 1-24 µg, for example 2-24 µg, for example 2 to 15 µg, human derived recombinant FSH. Preferably the dose is, or is equivalent to, 4.5 to 12.5 µg, for example 5 to 12.5 µg, for example 6 to 12.5 µg, for example 6.3 to 12 µg, human derived recombinant FSH.

According to the present invention in a further aspect there is provided a method of treatment of infertility comprising: (a) determining (e.g. measuring) the serum AMH level of a subject; and (b) administering a (e.g. daily) dose of, or dose equivalent to, 9 to 14 µg, for example 11 to 13 µg, for example 12 µg human derived recombinant follicle stimulating hormone (FSH) to a (the) subject having serum AMH level of <15 pmol/L (e.g. 0.05 pmol/L to 14.9 pmol/L). Preferably the FSH is a recombinant FSH ("rFSH" or "recFSH"). Preferably the FSH is a human cell line derived recombinant FSH. The dose provides an effective response while minimising risk of OHSS.

According to the present invention in a further aspect there is provided a method of treatment of infertility comprising: (a) determining (e.g. measuring) the serum AMH level of a subject; and (b) administering a (e.g. daily) dose of, or dose equivalent to, 5 to 12.5 µg human derived recombinant follicle stimulating hormone (FSH) to a (the) subject having serum AMH level of ≥15 pmol/L. The (e.g. daily) dose may be, or be equivalent to, 6 to 10 µg human derived recombinant follicle stimulating hormone (FSH). Preferably the FSH is a recombinant FSH ("rFSH" or "recFSH"). Preferably the FSH is a human cell line derived recombinant FSH. The dose provides an effective response while minimising risk of OHSS.

In one embodiment, the method includes a step of administering a (e.g. daily) dose of, or dose equivalent to, 5 to 12 µg, for example 7 to 12 µg, for example 8.7 to 10 µg, human derived recombinant FSH (preferably 9 to 10 µg human derived recombinant FSH) to a (the) subject having serum AMH level of 15 to 24.9 pmol/L In another embodiment, the method includes a step of administering a (e.g. daily) dose of, or dose equivalent to, 5 to 12 µg human derived recombinant FSH (for example 7 to 12 µg, for example 6 to 9 µg, for example 7 to 8 µg, for example 7.3 to 8 µg human derived recombinant FSH) to a (the) subject having serum AMH level of 25 to 34.9 pmol/L. In another embodiment, the method includes a step of administering a (e.g. daily) dose of, or dose equivalent to, 5 to 11 µg human derived recombinant FSH (for example 6 to 7 µg, for example 6.3 to 7 µg, human derived recombinant FSH) to a (the) subject having serum AMH level of ≥35 pmol/L.

According to the present invention in a further aspect there is provided a method of treatment of infertility comprising: (a) determining (e.g. measuring) the serum AMH level of a subject; and (b) administering a (e.g. daily) dose of, or dose equivalent to, 0.09 to 0.19 µg (for example 0.09 to 0.17 µg) human derived recombinant FSH per kg bodyweight of the subject, wherein the subject has serum AMH level of ≥15 pmol/L. Preferably the FSH is a recombinant FSH ("rFSH" or "recFSH"). Preferably the FSH is a human cell line derived recombinant FSH. The dose provides an effective response while minimising risk of OHSS.

In one embodiment, the method includes a step of administering a (e.g. daily) dose of, or dose equivalent to, 0.14 to 0.19 µg human derived recombinant FSH (preferably 0.15 to 0.16 µg human derived recombinant FSH) per kg bodyweight of the subject, the subject having serum AMH level of 15 to 24.9 pmol/L . In another embodiment, the method includes a step of administering a (e.g. daily) dose of, or dose equivalent to, 0.11 to 0.14 µg human derived recombinant FSH (preferably 0.12 to 0.13 µg human derived recombinant FSH) per kg bodyweight of the subject, the subject having serum AMH level of 25 to 34.9 pmol/L. In another embodiment, the method includes a step of administering a (e.g. daily) dose of, or dose equivalent to, 0.10 to 0.11 µg human derived recombinant FSH per kg bodyweight of the subject, the subject having serum AMH level of ≥35 pmol/L. Preferably the FSH is a recombinant FSH ("rFSH" or "recFSH"). Preferably the FSH is a human cell line derived recombinant FSH. These doses provide an effective response while minimising risk of OHSS.

According to the present invention in a further aspect there is provided a method of treatment of infertility comprising: (a) determining (e.g. measuring) the serum AMH level of a subject; and (b) administering a (e.g. daily) dose of, or dose equivalent to, 0.15 to 0.21 µg (for example 0.19 to 0.21 µg) human derived recombinant FSH per kg bodyweight of the subject, wherein the subject has serum AMH level of <15 pmol/L.

The administration preferably comprises a daily dose of, or a daily dose equivalent to, the amount of FSH defined above and in the claims. The (daily) dose may be an initial dose (it may be reduced, increased, or maintained during the treatment).

The method may be a method of treatment of infertility in the patient's (subject's) first stimulation protocol. It will be appreciated that for further stimulation cycles, the doses may be adjusted according to actual ovarian response in the first cycle.

According to the present invention in a further aspect there is provided a method of treatment of infertility comprising: (a) determining (e.g. measuring) the serum AMH level of a subject;

and (b) if the subject has serum AMH level of <15 pmol/L (e.g. 0.05 pmol/L to 14.9 pmol/L), administering to the subject a dose of, or dose equivalent to, 10 to 14 µg, for example 11 to 13 µg, for example 12 µg, human derived recombinant follicle stimulating hormone (FSH); or if the subject has serum AMH level of 15 to 24.9 pmol/L, administering to the subject a dose of, or dose equivalent to, 0.14 to 0.19 µg human derived recombinant FSH (preferably 0.15 to 0.16 µg human derived recombinant FSH) per kg bodyweight of the subject; or if the subject has serum AMH level of 25 to 34.9 pmol/L pmol/L, administering to the subject a dose of, or dose equivalent to, 0.11 to 0.14 µg human derived recombinant FSH (preferably 0.12 to 0.13 µg human derived recombinant FSH) per kg bodyweight of the subject; or if the subject has serum AMH level of ≥35 pmol/L pmol/L, administering to the subject a dose of, or dose equivalent to, 0.10 to 0.11 µg human derived recombinant FSH per kg bodyweight of the subject.

For a patient (subject) having serum AMH of 5.0-14.9 pmol/L, a dose of, or dose equivalent to, 6 to 18 µg, for example 8 to 11 µg, for example 8.5 to 10.2 µg human derived recombinant FSH may be administered. For a patient (subject) having serum AMH 15.0-29.9 pmol/L, a dose of, or a dose equivalent to, 4.8 to 15 µg, for example 6 to 9 µg, for example 6.8 to 8.5 µg human derived recombinant FSH may be administered. For a patient (subject) having serum AMH 30-44.9 pmol/L, a dose of, or a dose equivalent to, 3.6 to 12 µg, for example 4 to 7 µg, for example 5.1 to 6.8 µg human derived recombinant FSH may be administered. For a patient (subject) having serum AMH 45 pmol/L or greater, a dose of, or a dose equivalent to, 2 to 9 µg, for example 2.4 to 9 µg (for example 3.4 to 5.1 µg) or 2 to 5 µg human derived recombinant FSH may be administered. For a patient (subject) having serum AMH of 5 pmol/L or less, a dose of, or a dose equivalent to 7.2 to 24 µg, for example 10 to 15 µg for example 10.2 to 13.6 µg, human derived recombinant FSH may be administered. In some examples, a dose of, or dose equivalent to, 4.8 to 18 µg, for example 6 to 11 µg, for example 6.8 to 10.2 µg human derived recombinant FSH is administered. Preferably the FSH is a recombinant FSH ("rFSH" or "recFSH"). Preferably the FSH is a human cell line derived recombinant FSH.

The administration preferably comprises a daily dose of, or a daily dose equivalent to, the amount of FSH defined above and in the claims. The (daily) dose may be an initial dose (it may be reduced, increased, or maintained during the treatment.

DETAILED DESCRIPTION OF THE INVENTION

The present invention will now be described in more detail with reference to the attached drawings in which.

SEQUENCE SELECTION

Human FSH

The coding region of the gene for the FSH alpha polypeptide was used to according to Fiddes and Goodman. (1981). The sequence is banked as AH007338 and at the time of construction there were no other variants of this protein sequence. The sequence is referred herein as SEQ ID NO:1.

The coding region of the gene for FSH beta polypeptide was used according to Keene et al (1989). The sequence is banked as NM_000510 and at the time of construction there were no other variants of this protein sequence. The sequence is referred herein as SEQ ID NO: 2

Sialyltransferase

α2,3-Sialyltransferase—The coding region of the gene for beta-galactoside alpha-2,3-sialyltransferase 4 (α2,3-sialyltransferase, ST3GAL4) was used according to Kitagawa and Paulson (1994). The sequence is banked as L23767 and referred herein as SEQ ID NO: 3.

α2,6-Sialyltransferase—The coding region of the gene for beta-galactosamide alpha-2,6-sialyltransferase 1 (α2,6-sialyltransferase, ST6GAL1) was used according to Grundmann et al. (1990). The sequence is banked as NM_003032 and referred herein as SEQ ID NO: 4.

EXAMPLES

Example 1

Construction of the FSH Expression Vector

The coding sequence of FSH alpha polypeptide (AH007338, SEQ ID NO: 1) and FSH beta polypeptide (NM_003032, SEQ ID NO: 2) were amplified by PCR using the primer combinations FSHa-fw and FSHa-rev and FSHb-fw and FSHb-rec respectively.

```
FSHa-fw
                                      (SEQ ID NO: 9)
5'-CCAGGATCCGCCACCATGGATTACTACAGAAAAATATGC-3'

FSHa-rev
                                     (SEQ ID NO: 10)
5'-GGATGGCTAGCTTAAGATTTGTGATAATAAC-3'

FSHb-fw
                                     (SEQ ID NO: 11)
5'-CCAGGCGCGCCACCATGAAGACACTCCAGTTTTTC-3'

FSHb-rev
                                     (SEQ ID NO: 12)
5'-CCGGGTTAACTTATTATTCTTTCATTTCACCAAAGG-3'
```

The resulting amplified FSH beta DNA was digested with the restriction enzymes AscI and HpaI and inserted into the AscI and HpaI sites on the CMV driven mammalian expression vector carrying a neomycin selection marker. Similarly the FSH alpha DNA was digested with BamHI and NheI and inserted into the sites BamHI and NheI on the expression vector already containing the FSH beta polypeptide DNA.

Figure 1:
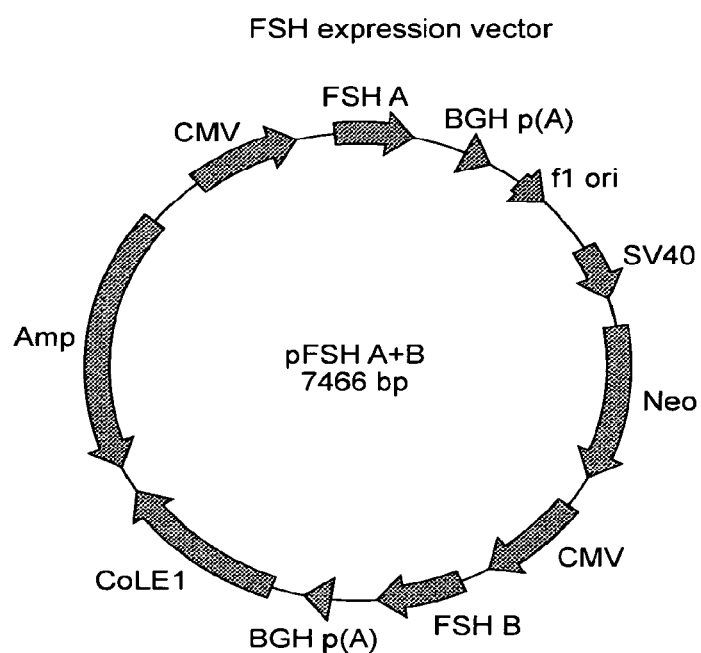
FIG. 1 shows a plasmid map of the pFSHalpha/beta expression vector.

The vector DNA was used to transform the DH5α strain of *E.coli*. Colonies were picked for amplification. Colonies containing the vector containing both FSH alpha and beta were selected for sequencing and all contained the correct sequences according to SEQ ID NO: 1 and SEQ ID NO: 2. Plasmid pFSH A+B#17 was selected for transfection (FIG. 1).

Example 2

Construction of the ST3 Expression Vector

The coding sequence of beta-galactoside alpha-2,3-sialyltransferase 4 (ST3, L23767, SEQ ID NO: 3) was amplified by PCR using the primer combination 2,3STfw and 2,3ST-rev.

```
2, 3STfw
                                     (SEQ ID NO: 13)
5'-CCAGGATCCGCCACCATGTGTCCTGCAGGCTGGAAGC-3'

2, 3STrev
                                     (SEQ ID NO: 14)
5'-TTTTTTTCTTAAGTCAGAAGGACGTGAGGTTCTTG-3'
```

The resulting amplified ST3 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST3#1 (FIG. 2) contained the correct sequence according SEQ ID NO: 3 and was selected for transfection.

Example 3

Construction of the ST6 Expression Vector

The coding sequence of beta-galactosamide alpha-2,6-sialyltransferase 1 (ST6, NM_003032, SEQ ID NO: 4) was amplified by PCR using the primer combination 2,6STfw and 2,6STrev.

```
2, 6STfw
                                     (SEQ ID NO: 15)
5'-CCAGGATCCGCCACCATGATTCACACCAACCTGAAG-3'

2, 6STrev
                                     (SEQ ID NO: 16)
5'-TTTTTTTCTTAAGTTAGCAGTGAATGGTCCGG-3'
```

The resulting amplified ST6 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST6#11 (FIG. 3) contained the correct sequence according SEQ ID NO: 4 and was selected for transfection.

Example 4

Stable Expression of pFSH α+β in PER.C6® cells. Transfection Isolation and Screening of Clones PER.C6®clones producing FSH were generated by expressing both polypeptide chains of FSH from a single plasmid (see Example 1).

To obtain stable clones a liposome based transfection agent with the pFSH α+β construct. Stable clones were selected in VPRO supplemented with 10% FCS and containing G418. Three weeks after transfection G418 resistant clones grew out. Clones were selected for isolation. The isolated clones were cultured in selection medium until 70-80% confluent. Supernatants were assayed for FSH protein content using an FSH selective ELISA and pharmacological activity at the FSH receptor in cloned cell line, using a cAMP accumulation assay. Clones expressing functional protein were progressed for culture expansion to 24 well, 6 well and T80 flasks.

Studies to determine productivity and quality of the material from seven clones were initiated in T80 flasks to generate sufficient material. Cells were cultured in supplemented media as previously described for 7 days and the supernatant harvested. Productivity was determined using the FSH selective ELISA. The isoelectric profile of the material was determined by Isoelectric focusing (IEF), by methods known in the art. Clones with sufficient productivity and quality were selected for sialyltransferase engineering.

Example 5

Level of Sialylation is Increased in Cells that over Express α2,3-sialyltransferase. Stable Expression of pST3 in FSH Expressing PER.C6® Cells; Transfection Isolation and Screening of Clones PER.C6® clones producing highly sialylated FSH were generated by expressing α2,3 sialyltransferase from separate plasmids (Example 2) in PER.C6® cells already expressing both polypeptide chains of FSH (from Example 4). Clones produced from PER.C6® cells as set out in Example 4 were selected for their characteristics including productivity, good growth profile, production of functional protein, and produced FSH which included some sialylation. Stable clones were generated as previously described in Example 4. Clones were isolated, expanded and assayed. The α2,3-sialyltransferase clones were adapted to serum free media and suspension conditions.

As before, clones were assayed using a FSH selective ELISA, functional response in an FSH receptor cell line, IEF, metabolic clearance rate and Steelman Pohley analysis. Results were compared to a commercially available recombinant FSH (Gonal-f, Serono) and the parental FSH PER.C6®cell lines. FSH produced by most of the clones has significantly improved sialylation (i.e. on average more FSH isoforms with high numbers of sialic acids) compared to FSH expressed without α2,3-sialyltransferase. In conclusion expression of FSH together with sialyltransferase in PER.C6®cells resulted in increased levels of sialylated FSH compared to cells expressing FSH only.

Example 6

Production and Purification Overview

A procedure was developed to produce FSH in PER.C6®cells that were cultured in suspension in serum free medium. The procedure is described below and was applied to several FSH-producing PER.C6®cell lines.

FSH from α2,3-clone (Example 5) was prepared using a using a modification of the method described by Lowry et al. (1976).

For the production of PER.C6®-FSH, the cell lines were adapted to a serum-free medium, i.e., Excel 525 (JRH Biosciences). The cells were first cultured to form a 70%-90% confluent monolayer in a T80 culture flask. On passage the cells were re-suspended in the serum free medium, Excel 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $>1 \times 10^6$ cells/ml, the cells were sub-cultured to a cell density of 0.2 or $0.3 \times 10^6$ cells/ml and further cultured in shaker flasks at 37° C., 5% $CO_2$ and 100 rpm.

For the production of FSH, the cells were transferred to a serum-free production medium, i.e., VPRO (JRH Biosciences), which supports the growth of PER.C6®cells to very high cell densities (usually $>10^7$ cells/ml in a batch culture). The cells were first cultured to $>1 \times 10^6$ cells/ml in Excel 525, then spun down for 5 min at 1000 rpm and subsequently suspended in VPRO medium+6 mM L-glutamine to a density of $1 \times 10^6$ cells/ml. The cells were then cultured in a shaker flask for 7-10 days at 37° C., 5% $CO_2$ and 100 rpm. During this period, the cells grew to a density of $>10^7$ cells/ml. The culture medium was harvested after the cell viability started to decline. The cells were spun down for 5 min at 1000 rpm and the supernatant was used for the quantification and purification of FSH. The concentration of FSH was determined using ELISA (DRG EIA 1288).

Thereafter, purification of FSH was carried out using a modification of the method described by Lowry et al. (1976). Purification using charge selective chromatography was carried out to enrich the highly sialylated forms by methods well known in the art.

During all chromatographic procedures, enrichment of the sialylated forms of FSH as claimed herein was confirmed by RIA (DRG EIA 1288) and/or IEF.

Example 7

Quantification of Relative Amounts of α2,3 and α2,6 Sialic Acid

The relative percentage amounts of α2,3 and α2,6 sialic acid on purified rFSH (Example 6) were measured using known techniques.

N-Glycans were released from the samples using PNGase F under denaturative conditions and then labelled with 2-aminobenzamide. Released glycan forms were then separated and analysed by Weak Anion Exchange (WAX) column for determination of charge distribution. Labelled glycans treated with 2,3,6,8 sialidase for determination of total sialic acid and 2,3 sialidase for determination of 2,3 sialic acid, were further analyzed by wax column.

Figure 4:
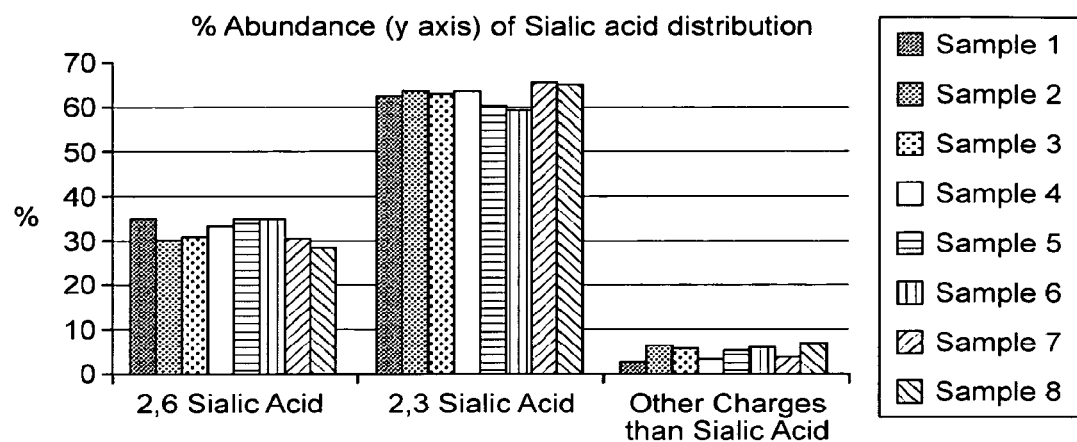
FIG. 4 shows % abundance sialic acid distribution of examples of recombinant FSH produced by PER.C6® cells stably expressing FSH after engineering with α2,3-sialyltransferase.

The relative percentages of the charged glycans were calculated from structures present in the undigested and digested glycan pools and are shown in FIG. 4 (for 8 samples). These were found to be in the ranges 50% -70% (e.g. about 60% or 65%) for α2,3 sialylation and 28 to 50%, generally 30 to 35% (e.g. about 31% or 35%), for α2,6 sialylation.

Example 8

Quantification of Relative Amounts Mono, di, tri and Tetra Sialylated Glycan Structures The relative percentage amounts of mono, di, tri and tetra sialylated structures on glycans extracted from purified rFSH (Example 6) were measured using known techniques.

Figure 5:
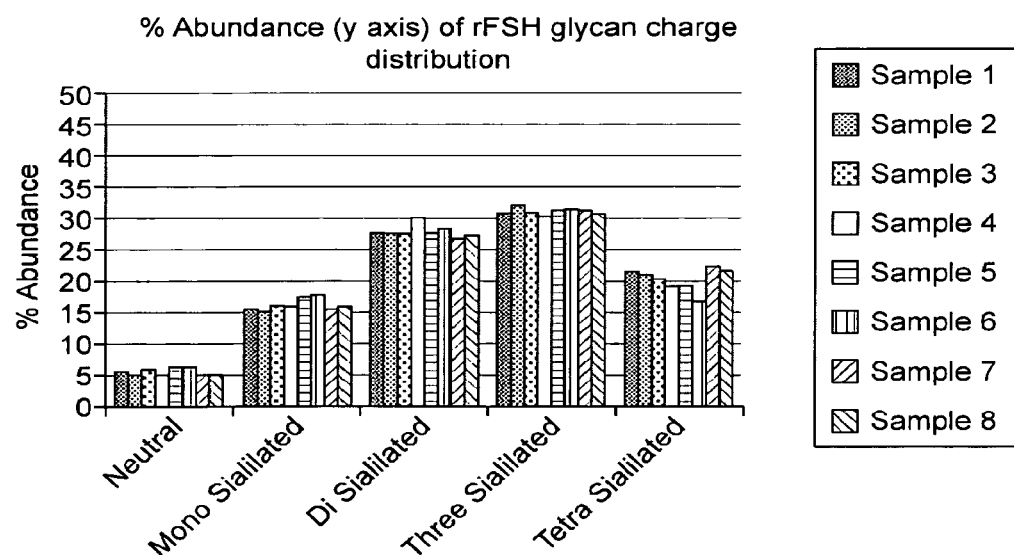
FIG. 5 shows % abundance of glycan charge distribution of examples of recombinant FSH produced by PER.C6® cells stably expressing FSH after engineering with α2,3-sialyltransferase.

N Glycans were released from the samples using PNGase F under denaturative conditions and then were labeled with 2-aminobenzamide. Glycans were released from the samples using PNGase F under denaturative conditions and then labeled with 2-aminobenzamide. Released glycan forms were then separated and analysed by Weak Anion Exchange (WAX) column for determination of sialylation distribution. The relative amounts of neutral, mono-sialylated, di-sialylated, tri-sialylated and tetra-sialylated structures are shown in FIG. 5 (for the 8 samples shown in FIG. 4).

The rFSH includes neutral, mono-sialylated, di-sialylated, tri-sialylated and tetra-sialylated glycan structures with relative amounts as follows: neutral 5-6%; 15-17% mono-sialylated; 26-30% di-sialylated; 30-32% tri-sialylated and 17-23% tetra-sialylated.

Example 8a

The relative percentage amounts of α2,6 sialic acid on purified rFSH extracted from nine samples of purified rFSH (produced by the methods of Example 6) were measured using known techniques.

N-Glycans were released from the samples using PNGase F under denaturative conditions and then labelled with 2-aminobenzamide. Released glycan forms were then separated and analysed by Weak Anion Exchange (WAX) column for determination of charge distribution. Labelled glycans treated with 2,3,6,8 sialidase for determination of total sialic acid and 2,3 sialidase for determination of 2,3 sialic acid, were further analyzed by wax column (see Example 8). The analysis allows calculation of α2,6 sialic acid.

The relative percentages of the charged glycans were calculated from structures present in the undigested and digested glycan pools and are shown in the following Table. These were found to be in the ranges 25 to 50%, generally 30 to 35% for α2,6 sialylation.

The relative percentage amounts of bisecting GlcNac, GalNac and 1-Fucose Lewis on glycans extracted from the nine samples of purified rFSH (produced by the methods of Example 6) were measured using known techniques. N-Glycans were released from the glycoprotrein using PNGase F and labeled with 2-aminobenzamide (2AB). The analysis was done by two dimensional (2D) HPLC analysis in combination with enzymatic degradation of the glycans. For verification, the glycans were analyzed by MALDI-MS The relative amounts of alpha 2,6-sialic acid and the terminal residues are shown in the following table, together with those for Gonal F (CHO cell derived recombinant FSH) and Bravelle (human urinary FSH).

following administration of FE 999049 compared to GONAL-F. Both number and size distribution of follicles showed a greater response to FE 999049 compared to GONAL-F.

Example 9 demonstrates that FSH having a specific amount (17-23%) of tetra-sialylated glycan structures and

| Sample | Ref. O abundance % | Ref. N abundance % | I-1 abundance % | I-2 abundance % | I-3 abundance % | II abundance % | II abundance % | III-1 abundance % | III-2 abundance % | Average abundance % | Gonal F abundance % | Bravelle abundance % |
|---|---|---|---|---|---|---|---|---|---|---|---|---|
| 2,6 sialic acid | 27.7 | 34.9 | 26.2 | 30.1 | 31.1 | 28.3 | 30.4 | 35 | 33 | 30.7 | 0 | 55.4 |
| 1GalNAc | 51 | 44.6 | 50.7 | 44.7 | 49 | 47.6 | 45.3 | 46.4 | 44.9 | 47.1 | 0 | 11.3 |
| Bisecting GlcNAc | 10 | 12.4 | 10.2 | 8.9 | 8.7 | 11.8 | 11.4 | 10.6 | 13.9 | 10.9 | 55 | 14 |
| 1 Fucose Lewis | 21.1 | 16.7 | 23.3 | 16.1 | 20.3 | 18.1 | 17.9 | 18.7 | 19.0 | 19.0 | 3.1[1] | 2.2 |
| 2 Fucose Lewis | 4 | 4.1 | 4.3 | 1.9 | 3.1 | 4.2 | 3.8 | 3.9 | 4.4 | 3.7 | — | n.d.[2] |

[1]Value of 3.1 is total ½ Fucose Lewis.
[2]Not determined.

It can be seen that the amount of GalNac in the FSH of the invention varies between about 44.9 and 51%, averaging about 47.1%.

It can be seen that the amount of bisecting GlcNac in the FSH of the invention varies between 8.7 and 13.9%, averaging approximately at 10.9%.

It can be seen that the amount of 1 Fucose Lewis in the FSH of the invention varies between 16.1 and 23.3%, averaging approximately at 19%.

It can be seen that the amount of 2 Fucose Lewis in the FSH of the invention varies between 1.9 and 4.4%, averaging approximately at 3.7%.

Example 9

A Multiple Dose Study Investigating the Safety, Tolerability, Pharmacokinetics, Pharmacodynamics, and Immunogenicity of FE 999049 in Comparison to GONAL-F Study Population A total of 48 (24 on each drug) healthy women received daily doses of 14.6 μg of FE 999049 (a composition according to the invention, produced according to Example 6) or 16.5 μg of Gonal-F for seven days.

Safety Results

Multiple dose administration of FE 999049 and GONAL-F was safe and generally well tolerated as assessed by Adverse Events (AEs), vital signs, ECG, clinical laboratory measurements, and physical examination. No serious adverse event or death occurred during the study.

Pharmacokinetic Results

Following the administration of FE 999049 and GONAL-F over 7 days, the FSH concentration values as assessed immediately prior to the next injection increased and seemed to reach a steady state level after 6-7 days. However the exposure (AUC and Cmax) of FE 999049 was 60% higher in comparison to Gonal-F.

Pharmacodynamic Results

Figure 6:
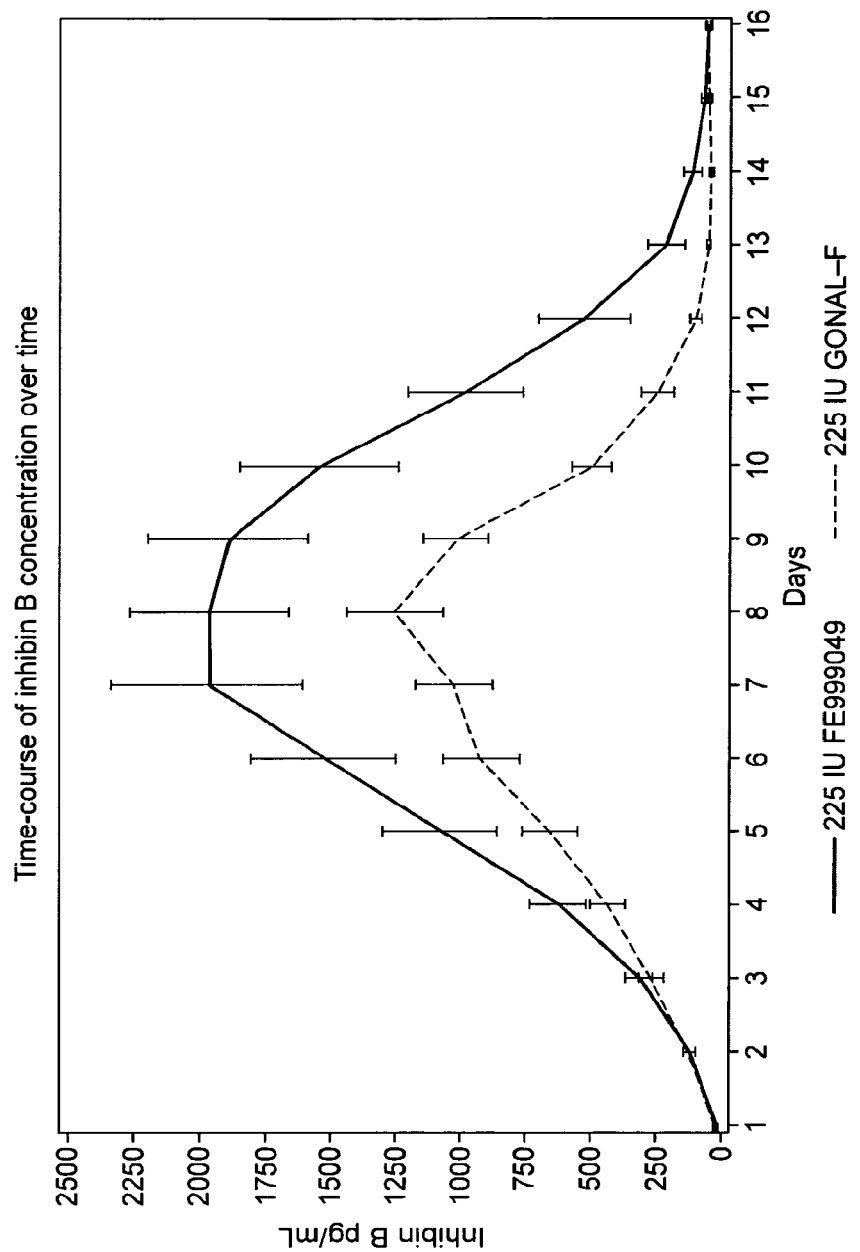
FIG. 6 shows a comparison of concentration of inhibin-B following administration of 225IU Gonal f (bottom line, dotted line) and 225 IU of the Example (top line, full line) of Invention.

The concentrations of inhibin-B (see FIG. 6), oestradiol, and progesterone all increased subsequent to administration of FE 999049 and GONAL-F, however to a greater extent e.g. specific amounts of α2,3 sialylation and α2,6 sialylation is markedly more potent then recombinant FSH products which are currently on the market.

Example 10

A Multiple Dose Study Investigating FE 999049 in Comparison to GONAL-F

The following describes a randomised, controlled, assessor-blind, parallel groups, multinational, multicentre trial assessing the dose-response relationship of FE 999049 in patients undergoing controlled ovarian stimulation for in vitro fertilisation (IVF)/intracytoplasmic sperm injection (ICSI). The patient population was 265 IVF patients aged between 18 to 37 years, with BMI 18.5 to 32.0 kg/m$^2$.

The trial was designed as a dose-response trial with number of oocytes retrieved as the primary endpoint. Secondary endpoints will explore the qualitative and quantitative impact of different doses of FE 999049 with regard to endocrine profile, follicular development, oocyte fertilisation, embryo quality and treatment efficiency (i.e. total gonadotropin consumption and duration of stimulation). The trial is designed to evaluate the efficacy of FE 999049 to establish pregnancy when used in controlled ovarian stimulation for IVF/ICSI cycles.

Subjects were assessed within 3 months prior to randomisation for compliance with the inclusion and exclusion criteria, including an anti-Müllerian hormone (AMH) assessment to increase homogeneity of the trial population in relation to ovarian response and minimise the number of potential poor and hyper-responders to the FE 999049 doses and GONAL-F dose used in the trial. The AMH assessment was measured using the AMH Gen-II enzyme linked immunosorbent assay kit (Beckman Coulter, Inc., Webster, Tex.). This assay can detect AMH concentrations greater than 0.57 pmol/L with a minimum limit of quantitation of 1.1 pmol/L.

On day 2-3 of their menstrual cycle, subjects were randomised in a 1:1:1:1:1:1 fashion to treatment with either 90 IU, 120 IU, 150 IU, 180 IU or 210 IU FE 999049 or 150 IU GONAL-F, and ovarian stimulation initiated. Randomisation was stratified according to AMH level at screening [5.0-14.9 pmol/L (low AMH) and 15.0 to 44.9 pmol/L (high AMH)).

Gonal-F is filled by mass (FbM) at FDA request; referring to μg dose is therefore appropriate. The Gonal –F label indicates 600 IU/44 μg, which indicates that 150 IU is 11 μg. However, there is some variation and the batch certificate for this trial indicated that 11.3 μg Gonal-F was equivalent to 150 IU. The FE999049 doses are presented by protein content (pg) rather than biological activity. Thus the doses of FE999049 were 5.2 μg (90 IU), 6.9 μg (120 IU), 8.6 μg (150 IU), 10.3 μg (180 IU) or 12.1 μg (210 IU).

The subject and dose distribution is set out as follows (data are number of subjects):

TABLE 1

|  | FE 999049 | | | | | GONAL-F | |
| --- | --- | --- | --- | --- | --- | --- | --- |
|  | 5.2 μg | 6.9 μg | 8.6 μg | 10.3 μg | 12.1 μg | 11.3 (11) μg | Total |
| Screened |  |  |  |  |  |  | 334 |
| Randomised and exposed | 42 | 45 | 44 | 45 | 46 | 43 | 265 |
| High AMH strata (15.0-44.9 pmol/L) | 23 | 26 | 24 | 24 | 26 | 25 | 148 (56%) |
| Low AMH strata (5.0-14.9 pmol/L) | 19 | 19 | 20 | 20 | 21 | 18 | 117 (44%) |
| Per-protocol | 40 | 42 | 42 | 44 | 44 | 43 | 255 |

The daily dose level of FE 999049 or GONAL-F is fixed throughout the entire stimulation period. During stimulation, subjects are monitored on stimulation day 1, 4 and 6 and hereafter at least every second day. When 3 follicles of ≥15 mm are observed, visits are performed daily. Subjects are treated with FE 999049 or GONAL-F for a maximum of 16 days.

To prevent a premature LH surge, a GnRH antagonist (ganirelix acetate, ORGALUTRAN, MSD/Schering-Plough) may be initiated on stimulation day 6 at a daily dose of 0.25 mg and continued throughout the stimulation period. Triggering of final follicular maturation is done on the day when follicles with a diameter ≥17 mm are observed. If there are <25 follicles with a diameter ≥12 mm, 250 μg recombinant hCG (choriogonadotropin alfa, OVITRELLE, Merck Serono/EMD Serono) is administered. If there are 25-35 follicles with a diameter ≥12 mm, 0.2 mg GnRH agonist (triptorelin acetate, DECAPEPTYL/GONAPEPTYL, Ferring Pharmaceuticals) is administered. In case of excessive ovarian response, defined as >35 follicles with a diameter ≥12 mm, the treatment is cancelled. In case of poor ovarian response, defined as <3 follicles with a diameter ≥10 mm observed on stimulation day 10, the cycle could be cancelled.

Oocyte retrieval takes place 36 h (±2 h) after triggering of final follicular maturation and the oocytes inseminated by IVF and/or ICSI. Fertilisation and embryo development are assessed from oocyte retrieval to the day of transfer. For subjects who underwent triggering of final follicular maturation with hCG, one blastocyst of the best quality available is transferred on day 5 after oocyte retrieval while remaining blastocysts are frozen. For subjects who undergo triggering of final follicular maturation with GnRH agonist, no embryo transfer takes place in the fresh cycle and blastocysts are instead frozen on day 5. Vaginal progesterone tablets (LUTINUS, Ferring Pharmaceuticals) 100 mg 3 times daily are provided for luteal phase support from the day after oocyte retrieval until the day of the clinical pregnancy visit. A βhCG test is performed 13-15 days after embryo transfer and clinical pregnancy will be confirmed by transvaginal ultrasound (TVU) 5-6 weeks after embryo transfer.

Results

The number of oocytes retrieved (primary endpoint) is shown in the following Table.

TABLE 2

| Oocytes retrieved | FE 999049 | | | | | GONAL-F |
| --- | --- | --- | --- | --- | --- | --- |
|  | 5.2 μg | 6.9 μg | 8.6 μg | 10.3 μg | 12.1 μg | 11.3 (11) μg |
| All | 5.2 (3.3) | 7.9 (5.9) | 9.2 (4.6) | 10.6 (7.0) | 12.2 (5.9) | 10.4 (5.2) |
| High AMH | 5.9 (3.9) | 9.1 (6.4) | 10.6 (4.8) | 13.6 (7.8) | 14.4 (5.8) | 12.4 (5.4) |
| Low AMH | 4.5 (2.2) | 6.3 (4.9) | 7.4 (3.8) | 6.9 (3.6) | 9.4 (4.9) | 7.8 (3.4) |

Data are mean (SD)

The primary objective was met: a significant dose-response relationship was established for FE 999049 with respect to number of oocytes retrieved. This finding was observed not only for the overall trial population, but also for each of the two AMH strata used at randomisation.

A significant dose-response for FE 999049 was demonstrated for all key objective pharmacodynamic parameters, e.g. estradiol, inhibin B and inhibin A. At a similar microgram dose level, the pharmacodynamic responses with FE 999049 were larger than with GONAL-F (these results not shown).

The serum FSH concentrations after exposure to FE 999049 were significantly higher than for GONAL-F. The results confirm that the PK profile of FE 999049 differs from that of GONAL-F. Fertilisation rates, blastocyst development and pregnancy rates in IVF/ICSI patients treated with FE 999049 were within expectations.

There were no safety concerns with the use of FE 999049. A good local tolerability was documented.

Further Analysis

The applicants have further analysed the data to identify the FE 999049 dose(s) that fulfil the following criteria with respect to number of oocytes retrieved:

Oocytes retrieved in the range 8-14
Minimise proportion of patients with <8 oocytes
Minimise proportion of patients with ≥20 oocytes The applicants also investigated the impact of body weight. If relevant, the dose is converted into µg/kg for an average subject. This value of µg/kg and ±0.01 µg/kg are evaluated in a model with respect to distribution of oocytes retrieved as well as safety profile, and the optimal dose is identified.

Low AMH Strata

As seen in Table 2, the dose of FE999049 which fulfilled the first criterion (Oocytes retrieved in the range 8-14) was 12.1 µg (mean 9.4 oocytes retrieved). The distribution of oocytes is shown in Table 3 below.

TABLE 3

| Oocytes retrieved | FE 999049 | | | | | GONAL-F |
|---|---|---|---|---|---|---|
| | 5.2 µg | 6.9 µg | 8.6 µg | 10.3 µg | 12.1 µg | 11.3 (11) µg |
| <4 | 32% | 24% | 15% | 10% | 10% | 6% |
| 4-7 | 63% | 42% | 45% | 60% | 20% | 56% |
| 8-14 | 5% | 24% | 35% | 30% | 60% | 33% |
| 15-19 | 0% | 5% | 5% | 0% | 5% | 6% |
| ≥20 | 0% | 5% | 0% | 0% | 5% | 0% |

Data are % of subjects

As shown by the box and arrow, a dose of 12.1 µg FE999049 provides retrieval of the most desirable number of oocytes in 60% of subjects in the low AMH group. This is a marked improvement on Gonal-F (most desirable number of oocytes in only 33% of subjects).

Table 4 below shows the analysis of signs of excessive response in the low AMH strata (data are number of subjects). It can be seen that there were no indications of early OHSS of a moderate or severe nature and there were no incidences of preventative action being required; there are no concerns associated with the dose of 12.1 µg FE999049 in a patient having low AMH.

TABLE 4

| | FE 999049 | | | | | GONAL-F |
|---|---|---|---|---|---|---|
| | 5.2 µg | 6.9 µg | 8.6 µg | 10.3 µg | 12.1 µg | 11.3 (11) µg |
| All subjects | 19 | 19 | 20 | 20 | 21 | 18 |
| Early OHSS, mod/sev | 0 | 0 | 0 | 0 | 0 | 0 |
| GnRH agonist triggering | 0 | 0 | 0 | 0 | 0 | 0 |
| Preventive action* | 0 | 0 | 0 | 0 | 0 | 0 |
| ≥15 oocytes | 0 | 2 | 1 | 0 | 2 | 1 |
| Any of the above | 0 | 2 | 1 | 0 | 2 | 1 |

Figure 7:
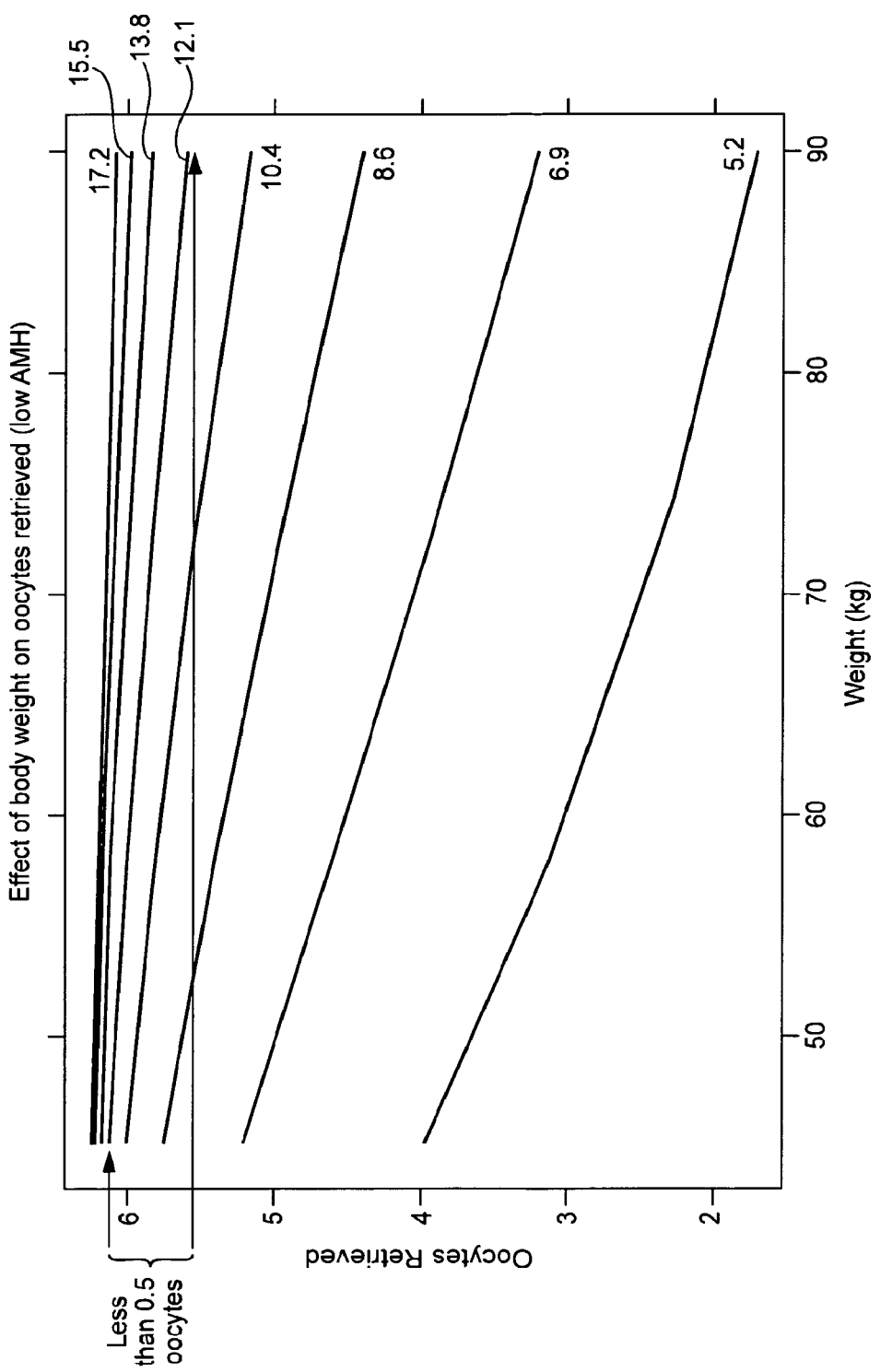
FIG. 7 shows the effect of body weight on oocytes retrieved in the low AMH treatment group (Example 10, 10A)

FIG. 7 shows the effect of body weight on oocytes retrieved (for the low AMH strata), for the various doses. The arrows indicate the number of oocytes retrieved from subjects of bodyweight between 45 kg and 90 kg treated at the 12.1 µg dose. As can be seen (text box) the variation between patients of bodyweight 45 kg and those of 90 kg is less than around 0.5 oocytes; in other words dosing by body weight is not required in patients with low AMH when dose of FE999049 is at least 12 µg, because there is not a significant variation in oocytes retrieved with body weight, at this dose.

Thus the applicants have found that a dose of, or dose equivalent to, 6 to 18 µg, for example 9 to 14 µg, for example 12 µg, human derived recombinant FSH is suitable for use in the treatment of infertility in a patient having serum AMH <15 pmol/L, for example 0.05-14.9 pmol/L for example 5.0-14.9 pmol/L. The dose provides an effective response while minimising risk of OHSS.

High AMH Strata

As seen in Table 2, three doses of FE999049 fulfilled the first criterion (oocytes retrieved in the range 8-14): 6.9 µg (mean 9.1 oocytes retrieved), 8.6 µg (mean 10.6 oocytes retrieved), and 10.3 µg (mean 13.6 oocytes retrieved).

Figure 8:
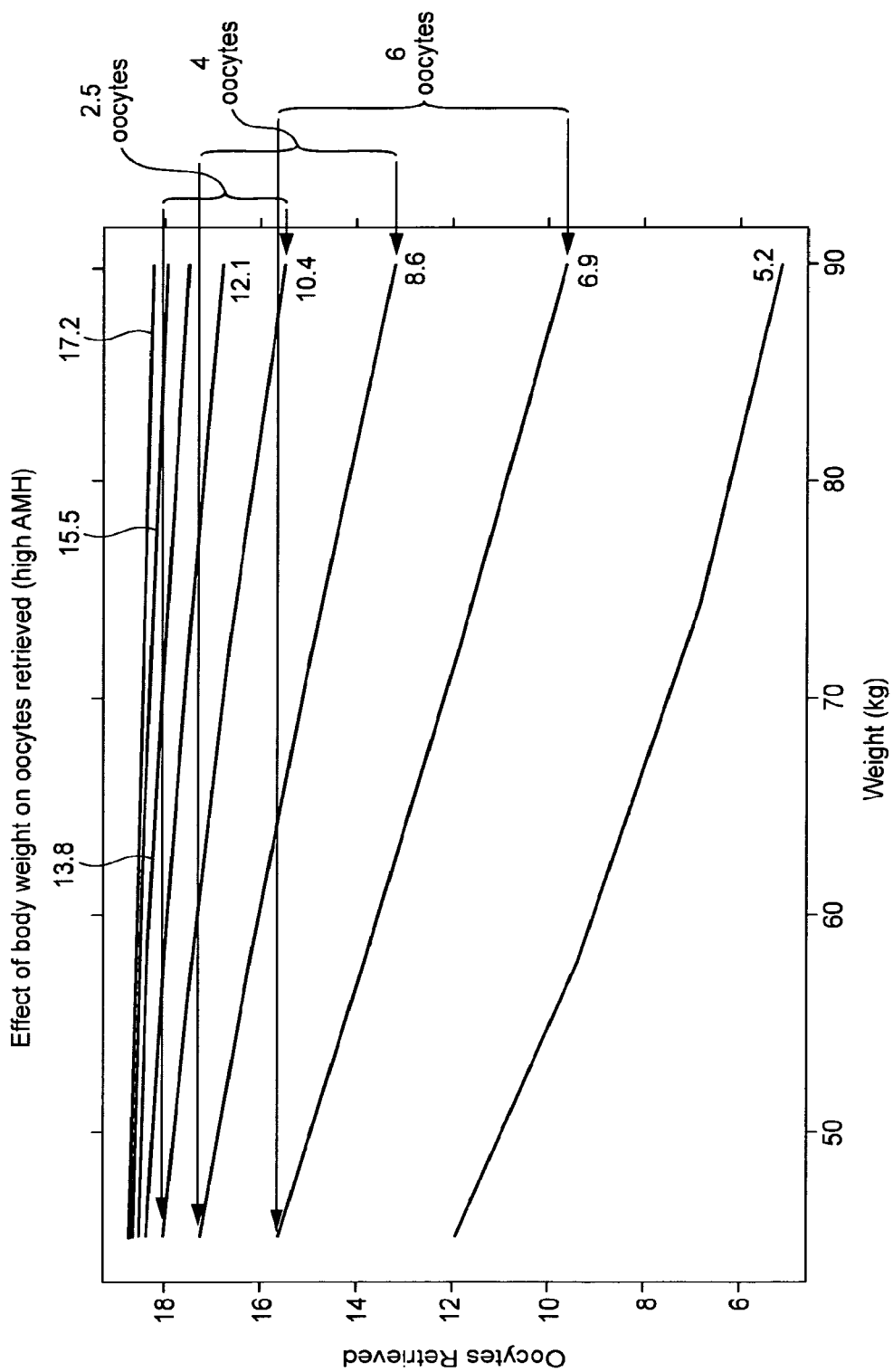
FIG. 8 shows the effect of Body weight on oocytes retrieved in the high AMH treatment group

FIG. 8 shows the effect of body weight on oocytes retrieved (for the high AMH strata), for the various doses. The arrows indicate the number of oocytes retrieved from subjects of body weight between 45 kg and 90 kg treated at the 6.9 µg, 8.6 µg and 10.3 µg doses. As can be seen (text boxes) the variation is significant: for the 6.9 µg dose 6 additional oocytes will be retrieved from a 45 kg patient compared to a 90 kg patient; for the 8.6 µg dose 4 additional oocytes will be retrieved from a 45 kg patient compared to a 90 kg patient; and for the 10.1 µg dose 2.5 additional oocytes will be retrieved from a 45 kg patient compared to a 90 kg patient. In other words dosing by body weight has an impact in patients with high AMH when the dose of FE999049 is less than 12 µg, because there is a significant variation in oocytes retrieved with body weight, at these doses.

Table 5a below shows a further breakdown of oocytes retrieved (from Table 2) by AMH. This shows the doses which fulfilled the first criterion (oocytes retrieved in the range 8-14) for each sub strata of AMH (boxes).

TABLE 5a

|  | FE 999049 | | | | |
| --- | --- | --- | --- | --- | --- |
|  | 5.2 µg | 6.9 µg | 8.6 µg | 10.3 µg | 12.1 µg |
| Oocytes retrieved | | | | | |
| 15-24 pmol/L | 4.9 (3.8) | 7.3 (3.6) | 10.6 (5.1) | 11.5 (6.7) | 12.3 (5.9) |
| 25-34 pmol/L | 7.0 (1.8) | 9.1 (6.8) | 9.7 (6.7) | 15.5 (6.4) | 16.7 (4.9) |
| 35-45 pmol/L | 8.5 (9.2) | 21.0 (1.4) | 11.3 (2.6) | 18.0 (12.2) | 15.7 (6.5) |

Table 5 b below shows the analysis of patients where treatment was cancelled due to either excessive response or agonist triggering, for these subgroups. For example, one patient in the 25-34 pmol/L AMH strata cancelled due to excessive response following the dose of 10.3 µg and one patient in the 25-34 pmol/L AMH strata cancelled due to excessive response following the dose of 12.1 µg; one patient in the 35-45 pmol/L AMH strata cancelled following agonist triggering following dose of 10.3 µg; and one patient in the 35-45 pmol/L AMH strata cancelled following agonist triggering following dose of 6.9 µg.

TABLE 5b

|  | FE 999049 | | | | |
| --- | --- | --- | --- | --- | --- |
|  | 5.2 µg | 6.9 µg | 8.6 µg | 10.3 µg | 12.1 µg |
| OHSS***, cancellation due to excessive response or agonist triggering**** | | | | | |
| 15-24 pmol/L | 0 | 0 | 0 | 0 | 0 |
| 25-34 pmol/L | 0 | 0 | 0 | 1*** | 1*** |
| 35-45 pmol/L | 0 | 1**** | 0 | 1**** | 0 |

It can be seen therefore that tailoring of dose by bodyweight (FIG. 8) and AMH level would be useful in the high AMH strata, to minimise cancellations and maximise oocyte retrieval.

The applicants have found that the following doses provide an effective response while minimising risk of OHSS (kg is kg body weight of patient).

| Serum AMH | dose | (Max dose) |
| --- | --- | --- |
| <15 pmol/L | 12 µg | (12 µg) |
| 15-24 pmol/L | 0.14-0.19 µg/kg, for example 0.15-0.16 µg/kg, preferably 0.15 µg/kg | (12 µg) |
| 25-34 pmol/L | 0.11-0.14 µg/kg; for example 0.12-0.13 µg/kg, preferably 0.13 µg/kg | (12 µg) |
| ≥35 pmol/L | 0.10-0.11 µg/kg, preferably 0.11 µg/kg | (12 µg) |

The following are appropriate if dosing by bodyweight is not desired.

| Serum AMH | dose | (Max dose) |
| --- | --- | --- |
| <15 pmol/L | 12 µg | 12 µg |
| 15-24 pmol/L | 9.3-10 µg | (12 µg) |
| 25-34 pmol/L | 7.3-8 µg | (12 µg) |
| ≥35 pmol/L | 6.3-7 µg | (12 µg) |

The following are appropriate if fewer categories of AMH are required.

| 4 AMH categories | | 3 AMH categories | | 2 AMH categories | | One dose | |
| --- | --- | --- | --- | --- | --- | --- | --- |
| AMH | Dose | AMH | Dose | AMH | Dose | AMH | Dose |
| <15 | 12 µg | <15 | 12 µg | <15 | 12 µg | — | 0.16 µg/kg |
| 15-24 | 0.15-0.16 µg/kg | 15-24 | 0.15-0.16 µg/kg | ≥15 | 0.14 µg/kg | | |
| 25-34 | 0.12-0.13 µg/kg | ≥25 | 0.12 µg/kg | | | | |
| ≥35 | 0.10-0.11 µg/kg | | | | | | |

The following are appropriate if dosing by bodyweight is not desired.

| 4 AMH categories | | 3 AMH categories | | 2 AMH categories | | One dose | |
| --- | --- | --- | --- | --- | --- | --- | --- |
| AMH | Dose | AMH | Dose | AMH | Dose | AMH | Dose |
| <15 | 12 µg | <15 | 12 µg | <15 | 12 µg | — | 9.3 µg or 10 µg |
| 15-24 | 9.3-10 µg | 15-24 | 9.3-10 µg | ≥15 | 8.7 µg | | |
| 25-34 | 7.3-8 µg | ≥25 | 7.3 µg | | | | |
| ≥35 | 6.3-7 µg | | | | | | |

Thus the applicants have found that a dose of, or dose equivalent to, 9 to 14 µg, for example 12 µg, human derived recombinant FSH is suitable for use in the treatment of infertility in a patient having serum AMH <15 pmol/L, for example 0.05-14.9 pmol/L for example 5.0-14.9 pmol/L. The dose provides an effective response while minimising risk of OHSS.

The applicants have found that a dose of, or dose equivalent to, 5 to 12.5 µg, for example 6 to 10.5 µg, human derived recombinant FSH is suitable for use in the treatment of infertility in a patient having serum AMH ≥15 pmol/L. The dose provides an effective response while minimising risk of OHSS.

The applicants have found that a (e.g. daily) dose of, or dose equivalent to, 0.09 to 0.19 µg human derived recombinant FSH per kg bodyweight of the patient is suitable for use in the treatment of infertility in a patient having serum AMH level of ≥15 pmol/L. The applicants have found that a (e.g. daily) dose of, or dose equivalent to, 0.14 to 0.19 µg human derived recombinant FSH (preferably 0.15 to 0.16 µg human derived recombinant FSH) per kg bodyweight of the patient is suitable for use in the treatment of infertility in a patient having serum AMH level of 15 to 24.9 pmol/L. The applicants have found that a (e.g. daily) dose of, or dose equivalent to, 0.11 to 0.14 µg human derived recombinant FSH (preferably 0.12 to 0.13 µg human derived recombinant FSH) per kg bodyweight of the patient is suitable for use in the treatment of infertility in a patient having serum AMH level of 25 to 34.9 pmol/L. The applicants have found that a (e.g. daily) dose of, or dose equivalent to, 0.10 to 0.11 µg human derived recombinant FSH per kg bodyweight of the patient is suitable for use in the treatment of infertility in a patient having serum AMH level of ≥35 pmol/L. These doses provide an effective response while minimising risk of OHSS.

The applicants have found that a (e.g. daily) dose of, or dose equivalent to, 0.15 to 0.21 µg (e.g. 0.16 µg) human derived recombinant FSH per kg bodyweight of the patient is suitable for use in the treatment of infertility in a patient having serum AMH level of <15 pmol/L, for example for the first stimulation cycle with human derived recombinant FSH. However, it is not required that patients are dosed by body weight at this level of AMH.

Example 10 A

Individualised COS Protocol (Low AMH)

The selected patients are about to undergo COS for in vitro fertilisation (IVF)/intracytoplasmic sperm injection (ICSI) by methods known in the art. The pre-treatment protocol includes assessment/screening of the patient's serum AMH using the AMH Gen-II enzyme linked immunosorbent assay kit (Beckman Coulter, Inc., Webster, Tex.). This assay can detect AMH concentrations greater than 0.57 pmol/L with a minimum limit of quantitation of 1.1 pmol/L. AMH may be measured using other Assay kits (e.g. available from Roche).

The COS protocol proceeds in the usual manner apart from administration of the initial dose of FE 999049 according to AMH level at screening. A patient with an AMH level of <14.9 pmol/L would be administered an initial daily dose of approximately 12 µg FE 999049, a human derived recombinant FSH product manufactured according to the method of Example 6. A patient with an AMH level of 15 to 24.9 pmol/L would receive an initial daily dose of 0.15 to 0.19 µg of the human derived recombinant FSH per kg bodyweight of the patient. A patient with an AMH level of 25 to 34.9 pmol/L would receive an initial daily dose of 0.11 to 0.13 µg of the human derived recombinant FSH per kg bodyweight of the patient. A patient with an AMH level of ≥35 pmol/L would receive an initial daily dose of 0.10 to 0.11 µg of the human derived recombinant FSH per kg bodyweight of the patient.

Example 11

Individualised COS Protocols

The doses in this protocol are less preferred that Example 10A.

The selected patients are about to undergo COS for in vitro fertilisation (IVF)/intracytoplasmic sperm injection (ICSI) by methods known in the art. The pre-treatment protocol includes assessment/screening of the patient's serum AMH using the AMH Gen-II enzyme linked immunosorbent assay kit (Beckman Coulter, Inc., Webster, Tex.). This assay can detect AMH concentrations greater than 0.57 pmol/L with a minimum limit of quantitation of 1.1 pmol/L.

The COS protocol proceeds in the usual manner apart from administration of the initial dose of FE 999049 according to AMH level at screening in line with the following table. Thus a patient with an AMH level of 5-14.8 pmol/L would be administered 180 IU FSH in the form of approximately 8-11 µg FE 999049, a human derived recombinant FSH product manufactured according to the method of Example 6. A patient with an AMH level of 30-44.9 pmol/L would be administered 120 IU FSH in the form of approximately 4-7 µg FE 999049, a human derived recombinant FSH product manufactured according to the method of Example 6. If the AMH level is not available, the patient recombinant would be administered 120-180 IU FSH in the form of approximately 6-11 µg FE 999049, a human derived recombinant FSH product manufactured according to the method of Example 6.

| AMH Level | Starting Dose FSH | Approx equivalent in µg |
| --- | --- | --- |
| <5 pmol/l | 210 IU | 10-15 µg |
| 5-14.9 pmol/l | 180 IU | 8-11 µg |
| >15-29.9 pmol/l | 150 IU | 6-9 µg |
| >30-44.9 pmol/l | 120 IU | 4-7 µg |
| >45 pmol/l | 90 IU | 2-5 µg |
| Not Available | 120-180 IU | 6-11 µg |

REFERENCES

Andersen C Y, Westergaard L G, and van Wely M. (2004). FSH isoform composition of commercial gonadotrophin preparations: a neglected aspect? Reprod Biomed Online. 9(2), 231-236.

Arey B J, Stevis P E, Deecher D C, Shen E S, Frail D E, Negro-Vilar A, and Lopez F J. (1997) Induction of promiscuous G protein coupling of the follicle-stimulating hormone (FSH) receptor: a novel mechanism for transducing pleiotropic actions of FSH isoforms. Mol Endocrinol. 11(5) 517-526.

Baenziger J U and Green E D. (1988). Pituitary glycoprotein hormone oligosaccharides: structure, synthesis and function of the asparagine-linked oligosaccharides on lutropin, follitropin and thyrotropin. Biochim Biophys Acta. 947(2), 287-306.

Bassett R M, and Driebergen R. (2005). Continued improvements in the quality and consistency of follitropin alfa, recombinant human FSH. Reprod Biomed Online. 10(2), 169-177.

Damían-Matsumura P, Zaga V, Maldonado A, Sanchez-Hernández C, Timossi C, and Ulloa-Aguirre A. (1999). Oestrogens regulate pituitary alpha2,3-sialyltransferase messenger ribonucleic acid levels in the female rat. J Mol Endocrinol. 23(2), 153-165.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Dalpathado D S, Irungu J, Go E P, Butnev V Y, Norton K, Bousfield GR, and Desaire H. (2006). Comparative glycomics of the glycoprotein follicle stimulating hormone: glycopeptide analysis of isolates from two mammalian species. Biochemistry. 45(28), 8665-8673. No copy Dias J A, Van Roey P. (2001). Structural biology of human follitropin and its receptor. Arch Med Res. 32(6), 510-519

Fiddes, J. C. and Goodman, H. M. (1979) Isolation, cloning and sequence analysis of the cDNA for the alpha-subunit of human chorionic gonadotropin. Nature, 281, 351-356.

Flack, M. R., Bennet, A. P., Froehlich, J. Anasti, J N and Nisula, B. (1994). Increased biological activity due to basic isoforms in recombinant human follicle-stimulating hormone produced in a human cell line. J. Clin. Endocrinol. Metab., 79, 756-760

Fox K M, Dias J A, and Van Roey P. (2001). Three-dimensional structure of human follicle-stimulating hormone. Mol Endocrinol. 15(3), 378-89

Grabenhorst E, Hoffmann A, Nimtz M, Zettlmeissl G, and Conradt H S. (1995). Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal(beta 1-4)GlcNAc(beta 1-2)Man(alpha 1-3)-branch of diantennary oligosaccharides from secreted recombinant beta-trace protein. Eur J Biochem. 232(3) 718-25.

Green E D and Baenziger J U. (1988). Asparagine-linked oligosaccharides on lutropin, follitropin, and thyrotropin. II. Distributions of sulfated and sialylated oligosaccharides on bovine, ovine, and human pituitary glycoprotein hormones. J Biol Chem. 263(1) 36-44.

Grundmann,U., Nerlich,C., Rein,T. and Zettlmeissl, G. (1990). Complete cDNA sequence encoding human beta-galactoside alpha-2,6-sialyltransferase. G Nucleic Acids Res. 18 (3), 667

Howles, C. M. (1996). Genetic engineering of human FSH (Gonal-F). Hum Reprod. Update, 2,172-191.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Keene, J. L., Matzuk, M. M., Otani, T., Fauser, B,C,J,M., Galway, A. B., Hsueh, A. J. W. and Boime, I. (1989). Expression of Biologically active Human Follitropin in Chinese Hamster Ovary Cells. The Journal of Biological Chemistry, 264(9), 4769-4775.

Kitagawa,H. and Paulson, J.C (1994) Cloning of a novel alpha 2,3-sialyltransferase that sialylates glycoprotein and glycolipid carbohydrate groups. J. Biol. Chem. 269(2) 1394-1401.

Lee E U, Roth J, and Paulson JC (1989) Alteration of terminal glycosylation sequences on N-linked oligosaccharides of Chinese hamster ovary cells by expression of beta-galactoside alpha 2,6-sialyltransferase. J Biol Chem. 264(23) 13848-13855.

de Leeuw, R., Mulders, J., Voortman, G. Rombout, F. Damm, J. and Kloosterboer, L. (1996) Structure-function relationship of recombinant follicle stimulating hormone (Puregon). Mol. Hum. Reprod., 2, 361-369.

Lowry O H, Rosebrough N J, Farr A L, Randall R J. (1951) Protein measurement with the Folin phenol reagent. J Biol Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Olivennes F, Howles C M, Borini A, Germond M, Trew G, Wikland M, Zegers-Hochschild F, Saunders H (2009) Individualizing FSH dose for assisted reproduction using a novel algorithm: the CONSORT study. Reprod Biomed Online. 2009 Feb; 18 (2):195-204.

Pierce J G, and Parsons T F (1981) Glycoprotein hormones: structure and function Annu Rev Biochem. 50 465-495.

Pricer W E Jr, and Ashwell G. (1971). The binding of desialylated glycoproteins by plasma membranes of rat liver. J Biol Chem. 246(15), 4825-33.

Rathnam P, and Saxena B B. (1975). Primary amino acid sequence of follicle-stimulating hormone from human pituitary glands. I. alpha subunit. J Biol Chem.250(17):6735-6746.

Regoeczi E, Debanne M T, Hatton M C, and Koj A. (1978) Elimination of asialofetuin and asialoorosomucoid by the intact rat. Quantitative aspects of the hepatic clearance mechanism. Biochim Biophys Acta. 541(3), 372-84.

Royle L, Radcliffe C M, Dwek R A and Rudd P M (2006) Methods in Molecular Biology, ed I Brockhausen-Schutzbach (Humana Press), 347: Glycobiology protocols, 125-144.

Ryan R J, Keutmann H T, Charlesworth M C, McCormick D J, Milius R P, Calvo FO and Vutyavanich T. (1987). Structure-function relationships of gonadotropins. Recent Prog Horm Res.;43,:383-429.

Saxena B B and Rathnam P. (1976) Amino acid sequence of the beta subunit of follicle-stimulating hormone from human pituitary glands. J Biol Chem. 251(4), 993-1005

Steelman S L, and Pohley F M. (1953) Assay of the follicle stimulating hormone based on the augmentation with human chorionic gonadotropin. Endocrinology. 53(6), 604-616.

Steer C J, and Ashwell G. (1980) Studies on a mammalian hepatic binding protein specific for asialoglycoproteins. Evidence for receptor recycling in isolated rat hepatocytes. J Biol Chem. 255(7), 3008-13.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Timossi C M, Barrios de Tomasi J, Zambrano E, Gonzalez R, Ulloa-Aguirre A. (1998). A naturally occurring basically charged human follicle-stimulating hormone (FSH) variant inhibits FSH-induced androgen aromatization and tissue-type plasminogen activator enzyme activity in vitro. Neuroendocrinology. 67(3), 153-163.

Timossi C M, Barrios-de-Tomasi J, Gonzalez-Suarez R, Arranz MC, Padmanabhan V, Conn PM, and Ulloa-Aguirre A. (2000). Differential effects of the charge variants of human follicle-stimulating hormone. J Endocrinol. 165(2), 193-205.

Ulloa-Aguirre, A., Espinoza, R., Damian-Matsumura, P. and Chappel, S.C. (1988) Immunological and biological potencies of the different molecular species of gonadotrophins. Hum. Reprod. 3,491-501.

Ulloa-Aguirre, A., Cravioto, A., Damian-Matsunnura, P. Jimenez, M, Zambrano, E and Diaz-Sanchez, V. (1992) Biological characterization of the naturally occurring analogues of intrapituitary human follicle stimulating hormone. Hum. Reprod. 7,23-30.

Ulloa-Aguirre A, Midgley A R Jr, Beitins I Z, and Padmanabhan V. (1995). Follicle-stimulating isohormones: characterization and physiological relevance. Endocr Rev.16 (6), 765-787.

Ulloa-Aguirre A, Maldonado A, Damian-Matsunnura P, and Timossi C (2001). Endocrine regulation of gonadotropin glycosylation. Arch Med Res. 32(6), 520-532.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

Van Lenten L, and Ashwell G. (1972) The binding of desialylated glycoproteins by plasma membranes of rat liver. Development of a quantitative inhibition assay. J Biol Chem. 247(14), 4633-40.

Wide, L. and Albertsson-Wikland, K. (1990) Change in electrophoretic mobility of human follicle-stimulating hormone in serum after administration of gonadotropin-releasing hormone. J. Clin. Endocrinol. Metab. 70 271-276.

Wide, L. and Bakos, O. (1993). More basic forms of both human follicle-stimulating hormone and luteinizing hormone in serum at midcycle compared with the follicular or luteal phase. J. Clin. Endocrinol. Metab., 76 885-889.

Wide L, Naessén T, Sundström-Poromaa I, Eriksson K. (2007) Sulfonation and sialylation of gonadotropins in women during the menstrual cycle, after menopause, and with polycystic ovarian syndrome and in men. J Clin Endocrinol Metab.;92(11), 4410-4417.

Zambrano E, Zariñán T, Olivares A, Barrios-de-Tomasi J, and Ulloa-Aguirre A. (1999). Receptor binding activity and in vitro biological activity of the human FSH charge isoforms as disclosed by heterologous and homologous assay systems: implications for the structure-function relationship of the FSH variants. Endocrine. 10(2), 113-121.

Zhang X, Lok S H, and Kon O L (1998) Stable expression of human alpha-2,6-sialyltransferase in Chinese hamster ovary cells: functional consequences for human erythropoietin expression and bioactivity. Biochim Biophys Acta. 1425(3), 441-452.

Figure 2:
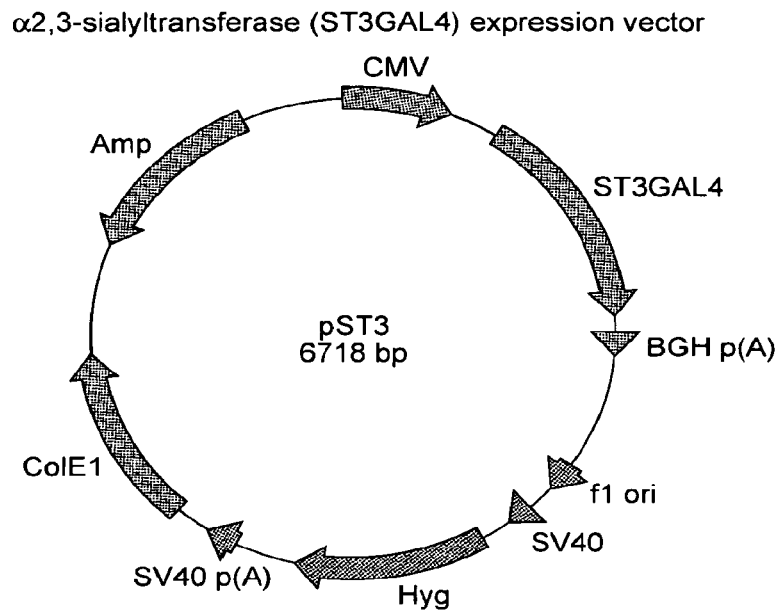
FIG. 2 shows the α2,3-sialyltransferase (ST3GAL4) expression vector.
Figure 3:
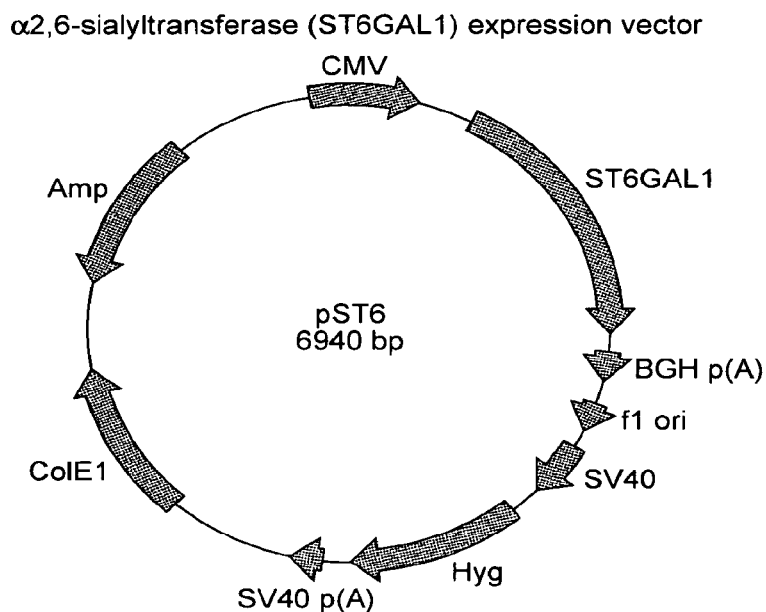
FIG. 3 shows the α2,6-sialyltransferase (ST6GAL1) expression vector.

FIGS. 1, 2 and 3: Plasmid maps of the pFSHalpha/beta, pST3 and pST6 expression vectors. CMV=Cytomegalovirus promoter, BGHp(A)=Bovine Growth Hormone poly-adenylation sequence, fl ori=fl origin of replication, SV40=Simian Virus 40 promoter, Neo=Neomycin resistance marker, Hyg=Hygromycin resistance marker, SV40 p(A)=Simian Virus 40 poly-adenylation sequence, FSH A=Follicle stimulating hormone alpha polypeptide, FSH B=Follicle stimulating hormone beta polypeptide, ST3GAL4=α2,3-sialyltransferase, ST6GAL1=α2,6-sialyltransferase, ColEI=ColEI origin of replication, Amp=ampicillin resistance marker.

SEQ ID NO: 1
Follicle stimulating hormone alpha polypeptide
Accession number AH007338
Nucleotide sequence of FSH alpha

```
  1 ATGGATTACT ACAGAAAATA TGCAGCTATC TTTCTGGTCA CATTGTCGGT GTTTCTGCAT
 61 GTTCTCCATT CCGCTCCTGA TGTGCAGGAT TGCCCAGAAT GCACGCTACA GGAAAACCCA
121 TTCTTCTCCC AGCCGGGTGC CCCAATACTT CAGTGCATGG GCTGCTGCTT CTCTAGAGCA
181 TATCCCACTC CACTAAGGTC CAAGAAGACG ATGTTGGTCC AAAAGAACGT CACCTCAGAG
241 TCCACTTGCT GTGTAGCTAA ATCATATAAC AGGGTCACAG TAATGGGGGG TTTCAAAGTG
301 GAGAACCACA CGGCGTGCCA CTGCAGTACT TGTTATTATC ACAAATCTTA A
```

Protein sequence of FSH alpha (SEQ ID NO: 5)

```
  1 MDYYRKYAAI FLVTLSVFLH VLHSAPDVQD CPECTLQENP FFSQPGAPIL QCMGCCFSRA
 61 YPTPLRSKKT MLVQKNVTSE STCCVAKSYN RVTVMGGFKV ENHTACHCST CYYHKS
```

SEQ ID NO: 2
Follicle stimulating hormone beta polypeptide
Accession number NM_000510
Nucleotide sequence of FSH beta

```
  1 ATGAAGACAC TCCAGTTTTT CTTCCTTTTC TGTTGCTGGA AAGCAATCTG CTGCAATAGC
 61 TGTGAGCTGA CCAACATCAC CATTGCAATA GAGAAAGAAG AATGTCGTTT CTGCATAAGC
121 ATCAACACCA CTTGGTGTGC TGGCTACTGC TACACCAGGG ATCTGGTGTA TAAGGACCCA
181 GCCAGGCCCA AAATCCAGAA AACATGTACC TTCAAGGAAC TGGTATATGA AACAGTGAGA
```

-continued

```
241 GTGCCCGGCT GTGCTCACCA TGCAGATTCC TTGTATACAT ACCCAGTGGC CACCCAGTGT
301 CACTGTGGCA AGTGTGACAG CGACAGCACT GATTGTACTG TGCGAGGCCT GGGGCCCAGC
361 TACTGCTCCT TTGGTGAAAT GAAAGAATAA
```

Protein sequence of FSH beta (SEQ ID NO: 6)

```
  1 MKTLQFFFLF CCWKAICCNS CELTNITIAI EKEECRFCIS INTTWCAGYC YTRDLVYKDP
 61 ARPKIQKTCT FKELVYETVR VPGCAHHADS LYTYPVATQC HCGKCDSDST DCTVRGLGPS
121 YCSFGEMKE
```

SEQ ID NO: 3
Beta-galactoside alpha-2,3-sialyltransferase 4
Accession Number L23767
Nucleotide sequence of ST3GAL4

```
  1 ATGTGTCCTG CAGGCTGGAA GCTCCTGGCC ATGTTGGCTC TGGTCCTGGT CGTCATGGTG
 61 TGGTATTCCA TCTCCCGGGA AGACAGGTAC ATCGAGCTTT TTTATTTTCC CATCCCAGAG
121 AAGAAGGAGC CGTGCCTCCA GGGTGAGGCA GAGAGCAAGG CCTCTAAGCT CTTTGGCAAC
181 TACTCCCGGG ATCAGCCCAT CTTCCTGCGG CTTGAGGATT ATTTCTGGGT CAAGACGCCA
241 TCTGCTTACG AGCTGCCCTA TGGGACCAAG GGGAGTGAGG ATCTGCTCCT CCGGGTGCTA
301 GCCATCACCA GCTCCTCCAT CCCCAAGAAC ATCCAGAGCC TCAGGTGCCG CCGCTGTGTG
361 GTCGTGGGGA ACGGGCACCG GCTGCGGAAC AGCTCACTGG GAGATGCCAT CAACAAGTAC
421 GATGTGGTCA TCAGATTGAA CAATGCCCCA GTGGCTGGCT ATGAGGGTGA CGTGGGCTCC
481 AAGACCACCA TGCGTCTCTT CTACCCTGAA TCTGCCCACT TCGACCCCAA AGTAGAAAAC
541 AACCCAGACA CACTCCTCGT CCTGGTAGCT TTCAAGGCAA TGGACTTCCA CTGGATTGAG
601 ACCATCCTGA GTGATAAGAA GCGGGTGCGA AAGGGTTTCT GGAAACAGCC TCCCCTCATC
661 TGGGATGTCA ATCCTAAACA GATTCGGATT CTCAACCCCT TCTTCATGGA GATTGCAGCT
721 GACAAACTGC TGAGCCTGCC AATGCAACAG CCACGGAAGA TTAAGCAGAA GCCCACCACG
781 GGCCTGTTGG CCATCACGCT GGCCCTCCAC CTCTGTGACT TGGTGCACAT TGCCGGCTTT
841 GGCTACCCAG ACGCCTACAA CAAGAAGCAG ACCATTCACT ACTATGAGCA GATCACGCTC
901 AAGTCCATGG CGGGGTCAGG CCATAATGTC TCCCAAGAGG CCCTGGCCAT TAAGCGGATG
961 CTGGAGATGG GAGCTATCAA GAACCTCACG TCCTTCTGA
```

Protein Sequence of ST3GAL4 (SEQ ID NO: 7)

```
  1 MCPAGWKLLA MLALVLVVMV WYSISREDRY IELFYFPIPE KKEPCLQGEA ESKASKLFGN
 61 YSRDQPIFLR LEDYFWVKTP SAYELPYGTK GSEDLLLRVL AITSSSIPKN IQSLRCRRCV
121 VVGNGHRLRN SSLGDAINKY DVVIRLNNAP VAGYEGDVGS KTTMRLFYPE SAHFDPKVEN
181 NPDTLLVLVA FKAMDFHWIE TILSDKKRVR KGFWKQPPLI WDVNPKQIRI LNPFFMEIAA
241 DKLLSLPMQQ PRKIKQKPTT GLLAITLALH LCDLVHIAGF GYPDAYNKKQ TIHYYEQITL
301 KSMAGSGHNV SQEALAIKRM LEMGAIKNLT SF
```

SEQ ID NO: 4
Beta-galactosamide alpha-2,6-sialyltransferase 1
Accession number NM_003032
Nucleotide sequence of ST6GAL1

```
   1 ATGATTCACA CCAACCTGAA GAAAAAGTTC AGCTGCTGCG TCCTGGTCTT TCTTCTGTTT
  61 GCAGTCATCT GTGTGTGGAA GGAAAAGAAG AAAGGGAGTT ACTATGATTC CTTTAAATTG
 121 CAAACCAAGG AATTCCAGGT GTTAAAGAGT CTGGGGAAAT TGGCCATGGG GTCTGATTCC
 181 CAGTCTGTAT CCTCAAGCAG CACCCAGGAC CCCCACAGGG GCCGCCAGAC CCTCGGCAGT
 241 CTCAGAGGCC TAGCCAAGGC CAAACCAGAG GCCTCCTTCC AGGTGTGGAA CAAGGACAGC
 301 TCTTCCAAAA ACCTTATCCC TAGGCTGCAA AAGATCTGGA AGAATTACCT AAGCATGAAC
 361 AAGTACAAAG TGTCCTACAA GGGGCCAGGA CCAGGCATCA AGTTCAGTGC AGAGGCCCTG
 421 CGCTGCCACC TCCGGGACCA TGTGAATGTA TCCATGGTAG AGGTCACAGA TTTTCCCTTC
 481 AATACCTCTG AATGGGAGGG TTATCTGCCC AAGGAGAGCA TTAGGACCAA GGCTGGGCCT
 541 TGGGGCAGGT GTGCTGTTGT GTCGTCAGCG GGATCTCTGA AGTCCTCCCA ACTAGGCAGA
 601 GAAATCGATG ATCATGACGC AGTCCTGAGG TTTAATGGGG CACCCACAGC CAACTTCCAA
 661 CAAGATGTGG GCACAAAAAC TACCATTCGC CTGATGAACT CTCAGTTGGT TACCACAGAG
 721 AAGCGCTTCC TCAAAGACAG TTTGTACAAT GAAGGAATCC TAATTGTATG GGACCCATCT
 781 GTATACCACT CAGATATCCC AAAGTGGTAC CAGAATCCGG ATTATAATTT CTTTAACAAC
 841 TACAAGACTT ATCGTAAGCT GCACCCCAAT CAGCCCTTTT ACATCCTCAA GCCCCAGATG
 901 CCTTGGGAGC TATGGGACAT TCTTCAAGAA ATCTCCCCAG AAGAGATTCA GCCAAACCCC
 961 CCATCCTCTG GGATGCTTGG TATCATCATC ATGATGACGC TGTGTGACCA GGTGGATATT
1021 TATGAGTTCC TCCCATCCAA GCGCAAGACT GACGTGTGCT ACTACTACCA GAAGTTCTTC
1081 GATAGTGCCT GCACGATGGG TGCCTACCAC CCGCTGCTCT ATGAGAAGAA TTTGGTGAAG
1141 CATCTCAACC AGGGCACAGA TGAGGACATC TACCTGCTTG GAAAAGCCAC ACTGCCTGGC
1201 TTCCGGACCA TTCACTGCTA A
```

Protein Sequence of ST6GAL1 (SEQ ID NO: 8)

```
  1 MIHTNLKKKF SCCVLVFLLF AVICVWKEKK KGSYYDSFKL QTKEFQVLKS LGKLAMGSDS
 61 QSVSSSSTQD PHRGRQTLGS LRGLAKAKPE ASFQVWNKDS SSKNLIPRLQ KIWKNYLSMN
121 KYKVSYKGPG PGIKFSAEAL RCHLRDHVNV SMVEVTDFPF NTSEWEGYLP KESIRTKAGP
181 WGRCAVVSSA GSLKSSQLGR EIDDHDAVLR FNGAPTANFQ QDVGTKTTIR LMNSQLVTTE
241 KRFLKDSLYN EGILIVWDPS VYHSDIPKWY QNPDYNFFNN YKTYRKLHPN QPFYILKPQM
301 PWELWDILQE ISPEEIQPNP PSSGMLGIII MMTLCDQVDI YEFLPSKRKT DVCYYYQKFF
361 DSACTMGAYH PLLYEKNLVK HLNQGTDEDI YLLGKATLPG FRTIHC
```

The invention claimed is:

1. A method of treating infertility by controlled ovarian stimulation, comprising administering follicle stimulating hormone (FSH) to a patient in need of such treatment, wherein the FSH is administered at a daily dose of, or a dose equivalent to a daily dose of, 0.10 to 0.11 μg recombinant FSH per kilogram bodyweight of the patient, wherein the patient has a serum anti-Mullerian hormone (AMH) level of ≥35 pmol/L.

2. The method of claim 1, wherein the method comprises a step of determining the serum AMH level of the patient, and a step of administering the dose of FSH to the patient having the serum AMH level of ≥35 pmol/L.

3. The method of claim 1, wherein the FSH includes α2,3- and α2,6-sialylation.

4. The method of claim 1, wherein the FSH is a human derived recombinant FSH.

5. A method of treating infertility by controlled ovarian stimulation, comprising administering follicle stimulating hormone (FSH) to a patient in need of such treatment, wherein the FSH is administered at a daily dose of, or a dose equivalent to a daily dose of, 0.10 to 0.11 μg recombinant FSH per kilogram bodyweight of the patient, wherein the patient is at risk of ovarian hyperstimulation syndrome (OHSS) and has a serum anti-Mullerian hormone (AMH) level of ≥35 pmol/L.

6. The method of claim 5, wherein the method comprises a step of determining the serum AMH level of the patient, and a step of administering the dose to the patient having the serum AMH level of ≥35 pmol/L.

7. The method of claim 5, wherein the FSH includes α2,3- and α2,6-sialylation.

8. The method of claim 5, wherein the FSH is a human derived recombinant FSH.

9. A method of treating infertility by controlled ovarian stimulation, comprising administering follicle stimulating hormone (FSH) to a patient in need of such treatment, wherein the patient is at risk of ovarian hyperstimulation syndrome (OHSS), and wherein the FSH is a human derived recombinant FSH and is administered at a daily dose of, or a dose equivalent to a daily dose of, 0.09 to 0.19 μg recombinant FSH per kilogram bodyweight of the patient.

10. The method of claim 9, wherein the treatment of infertility includes a step of determining the serum AMH level of the patient.

11. The method of claim 9, wherein the FSH includes α2,3- and α2,6-sialylation.

12. A method of treating infertility, the method comprising administering follicle stimulating hormone (FSH) to a patient in need of such treatment, wherein the FSH is administered at a daily dose of, or a dose equivalent to a daily dose of, 11-13 μg human derived recombinant FSH to the patient having a serum anti-Mullerian (AMH) hormone level of <15 pmol/L, and wherein the FSH is administered 12-16 days after administration of a gonadotrophin releasing hormone (GnRH) agonist.

13. The method of claim 12, wherein the method comprises a step of determining the serum AMH level of the patient, and a step of administering the dose of FSH to the patient having the serum AMH level of <15 pmol/L.

14. A method of treating infertility, the method comprising administering follicle stimulating hormone (FSH) to a patient in need of such treatment, wherein the FSH is administered at a daily dose of, or a dose equivalent to a daily dose of, 0.09-0.19 μg human derived recombinant FSH per kg bodyweight of the patient, to the patient having a serum anti-Mullerian (AMH) hormone level of ≥15 pmol/L, and wherein the FSH is administered 12-16 days after administration of a gonadotrophin releasing hormone (GnRH) agonist.

15. The method of claim 14, wherein the method comprises a step of determining the serum AMH level of the patient, and a step of administering the dose of FSH to the patient having the serum AMH level of ≥15 pmol/L.

* * * * *